(12) United States Patent
Takeuchi et al.

(10) Patent No.: US 6,878,492 B2
(45) Date of Patent: Apr. 12, 2005

(54) POLYMERIZABLE COMPOSITION AND USE THEREOF

(75) Inventors: Masataka Takeuchi, Chiba (JP); Shuichi Naijo, Chiba (JP); Ayako Nishioka, Chiba (JP)

(73) Assignee: Showa Denko Kabushiki Kaisha, Tokyo (JP)

( * ) Notice: Subject to any disclaimer, the term of this patent is extended or adjusted under 35 U.S.C. 154(b) by 226 days.

(21) Appl. No.: 09/901,122

(22) Filed: Jul. 10, 2001

(65) Prior Publication Data

US 2002/0018938 A1 Feb. 14, 2002

Related U.S. Application Data

(60) Provisional application No. 60/245,717, filed on Nov. 6, 2000.

(30) Foreign Application Priority Data

Jul. 10, 2000 (JP) ..................................... P2000-207828

(51) Int. Cl.[7] ................................................ H01M 6/18
(52) U.S. Cl. ..................... 429/317; 429/321; 429/322; 429/323; 429/337; 429/338; 429/341; 429/342; 429/343; 429/231.95; 252/62.2
(58) Field of Search ................................ 429/317, 324, 429/341, 342, 231.95, 321, 323, 337, 338, 343; 252/62.2

(56) References Cited

FOREIGN PATENT DOCUMENTS

| JP | 62-30147 | 2/1987 | |
|----|----------|--------|---|
| JP | 62-30148 | 2/1987 | |
| JP | 1-311573 | 12/1989 | |
| JP | 4-211412 | 8/1992 | |
| JP | 9-147912 | 6/1997 | |
| JP | 11-149823 | 6/1999 | |
| JP | 11-149824 | 6/1999 | |
| JP | 2000-67643 | 3/2000 | * |

* cited by examiner

Primary Examiner—Laura Weiner
(74) Attorney, Agent, or Firm—Sughrue Mion, PLLC

(57) ABSTRACT

The present invention provides a solid polymer electrolyte; a polymerizable composition having low viscosity and excellent processability for obtaining the solid polymer electrolyte; and a polymerizable compound having low viscosity, and good polymerizability and stability for use in the polymerizable composition. The present invention also provides primary and secondary batteries capable of working with high capacity and current; an electric double-layer capacitor ensuring high output voltage, large takeout current, and good processability; and an electrochromic device favored with high response speed. Each thereof use the solid polymer electrolyte of the present invention and are ensured with long life, excellent safety free of liquid leakage, high reliability and production at a low cost. A solid polymer electrolyte, including a carbonate-based polymer in which a branched chain is introduced and having a high dielectric constant and a wide electrochemical stability range, having excellent processability, good safety and high ionic conductivity, is provided.

18 Claims, 1 Drawing Sheet

POLYMERIZABLE COMPOSITION AND USE THEREOF

CROSS REFERENCE TO RELATED APPLICATIONS

This application is an application filed under 35 U.S.C. §111(a) claiming benefit pursuant to 35 U.S.C. §119(e)(1) of the filing date of Provisional Application No. 60/245,717 filed Nov. 6, 2000 pursuant to 35 U.S.C. §111(b).

FIELD OF THE INVENTION

The present invention relates to a highly ion conductive solid polymer electrolyte comprising a polymer compound containing a branched carbonate group as a main component and an electrolyte salt, which is useful for various electrochemical devices; a polymerizable compound and a polymerizable composition for obtaining the solid polymer electrolyte; and a battery, an electric double-layer capacitor and an electrochromic device using the solid polymer electrolyte.

BACKGROUND OF THE INVENTION

With the popularization of portable instruments in recent years, various batteries and capacitor devices such as electric double-layer capacitor are becoming lightweight and also, the production thereof is abruptly increasing. Furthermore, in view of the popularization in the future of hybrid car, electric car and the like, which are highly expected from an environmental aspect, there is a demand for capacitor devices to have larger size and higher performance. Among the batteries, nonaqueous batteries, such as Li primary battery and Li ion secondary battery are growing because of their high voltage and high energy density. Also, electric double-layer capacitors using an active carbon electrode having a high specific surface area as the polarizable electrode are also growing because of their high power density.

With respect to the display material, flatness and small thickness are being taken notice of and studies on improvements of liquid crystal, organic electroluminescent device and electrochromic (ECD) devices are aggressively proceeding. Among these, an ECD device exhibits color change by an electrochemical reaction, does not spontaneously emit light and is low in response speed. However, because of its memory property, the ECD device is attracting attention in view of its original purpose such as light-shielding glass, rather than as a display device.

These capacitor devices and ECD devices each uses an electrochemical reaction and the electrolyte material used therein is demanded to have higher performance. The properties required for the electrolyte material include high ionic conductivity, broad range of electrochemical stability, impregnation property into various electrodes, heat resistance, environmental resistance and safety. In particular, a Li (ion) battery, and a nonaqueous electric double-layer capacitor as a nonaqueous capacitor device are attracting attention at present because of their high voltage and high energy density. The electrolyte material used therefor is particularly demanded to satisfy the following requirements: to be improved in the ionic conductivity, to have an electrochemical stability range broad enough to endure high voltage use, to be easily compounded with various electrode materials and to have excellent safety.

Conventional liquid electrolytes have a problem in that the safety and reliability decrease due to liquid leakage or volatilization. In order to solve this problem, a solid polymer electrolyte obtained by solidifying an electrolyte salt with a polymer or the like is being taken notice of in recent years. Examples thereof include a solid polymer electrolyte characterized by the introduction of a polyether chain into a polymer (see, JP-A-4-211412 (the term "JP-A" as used herein means an "unexamined published Japanese patent application")). This solid polymer electrolyte is improved in safety and stability, but suffers from reduction in ionic conductivity or deterioration in the compounding property with various electrode materials and from a problem that when the solid polymer electrolyte is used in various electrochemical devices, the device has small takeout current.

In order to solve these problems of the solid polymer electrolyte, the present inventors have proposed a solid polymer electrolyte using a polymer having a carbonate structure, and a polymerizable compound and a polymerizable composition for obtaining the solid polymer electrolyte (see, for example, JP-A-11-149823 and JP-A-11-149824).

JP-A-1-311573 describes an electrochemical apparatus using a solid polymer electrolyte comprising a polymer having bonded thereto a side chain having no active hydrogen atom, where poly(ethylene ether carbonate) end capped with methacrylate is an example of the polymer.

JP-A-9-147912 describes a solid polymer electrolyte having both flexibility and rigidity, and improved in adhesive property to alkali electrode and in interface resistance by using a copolymer of poly(alkylene(ether)carbonate) end capped with methacrylate, similar to JP-A-1-311573, and a polyether end capped with methacrylate.

Also, JP-A-62-30147 and JP-A-62-30148 disclose a solid polymer electrolyte using polyalkylene carbonate having a specific structure, which enhances the compatibility of an organic solvent or an electrolyte salt and improves the mechanical properties.

The carbonate structure has a high dielectric constant and therefore, improves the solubility of electrolyte salt and compatibility with various organic solvents and in turn, the solid polymer electrolyte is improved in ionic conductivity. Furthermore, a broad electrochemical stability range is ensured, which is suited for the fabrication of devices having a high voltage. However, a polymer having a carbonate structure has a high viscosity compared with polyether-based polymers conventionally used for the polymer solid electrolyte and suffers from poor compounding property with various electrode materials.

SUMMARY OF THE INVENTION

An object of the present invention is to improve the processability and compounding property of a solid polymer electrolyte with an electrode of the carbonate-based polymer having high dielectric constant, high ionic conductivity and high electrochemical stability, thereby providing a solid polymer electrolyte favored with high ionic conductivity and excellent in durability, electrochemical stability, processability, safety and reliability.

Another object of the present invention is to provide a primary battery and a secondary battery facilitated in the formation into a thin film, broad in operation voltage, capable of working with high capacity and high current, favored with a long life and excellent in reliability and processability.

Still another object of the present invention is to provide an electric double-layer capacitor having high output voltage, large takeout current, good processability, long life and excellent reliability by using the above-described carbonate-based solid polymer electrolyte.

Still another object of the present invention is to provide an electrochromic device having good processability, high response speed, long life and excellent reliability by using the above-described carbonate-based solid polymer electrolyte.

As a result of extensive investigations to solve the above-described problems, the present inventors discovered that by introducing a branched chain into a carbonate chain to reduce the viscosity of a carbonate-based polymer, a solid polymer electrolyte having excellent processability can be obtained. Furthermore, when the carbonate-based polymer having introduced thereinto a branched chain is diluted with a solvent or the like to reduce the viscosity, a higher effect of reducing the viscosity can be brought out. This is presumed as resulting from the interaction between polymers being weakened by the introduction of a branched chain.

The present inventors also discovered that by polymerizing a low molecular weight polymerizable compound having a branched carbonate chain, a solid polymer electrolyte having excellent compounding property with an electrode material of various electrochemical devices can be obtained.

Still further, the present inventors discovered that by using the above-described solid polymer electrolyte, a primary battery and a secondary battery having broad operation voltage, capability of working with high capacity and high current, long life, no liquid leakage and excellent safety and reliability; an electric double-layer capacitor having high output voltage, large takeout current, good processability, long life, no liquid leakage and excellent safety and reliability; and an electrochromic device having high response speed, long life, no liquid leakage and excellent reliability can be obtained.

That is, the present invention provides a solid polymer electrolyte, a polymerizable compound composition for a solid polymer electrolyte, a battery, an electric double-layer capacitor and an electrochromic device using these, and provides the following embodiments.

(1) A solid polymer electrolyte comprising a polymer compound having a branched carbonate structure represented by formula (1) as a partial structure and at least one electrolyte salt:

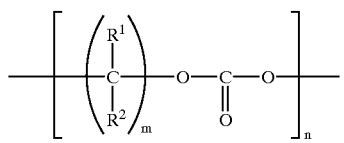
(1)

wherein $R^1$ and $R^2$ each represents a hydrogen atom, an alkyl group having from 1 to 10 carbon atoms, an alkoxy group having from 1 to 10 carbon atoms or an alkoxyalkyl group having from 1 to 10 carbon atoms, the alkyl, alkoxy or alkoxyalkyl group may have a linear, branched or cyclic structure, m represents an integer of 3 to 10, n represents an integer of 1 to 500, and $R^1$, $R^2$, m or n present in plurality within the same molecule may be the same or different, provided that $R^1$ or $R^2$ present in plurality within the same molecule are not a hydrogen atom at the same time.

(2) A solid polymer electrolyte comprising a polymer compound having a branched carbonate structure represented by formula (2) as a partial structure and at least one electrolyte salt:

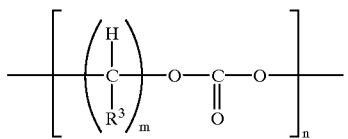
(2)

wherein $R^3$ represents a hydrogen atom, an alkyl group having from 1 to 10 carbon atoms, an alkoxy group having from 1 to 10 carbon atoms or an alkoxyalkyl group having from 1 to 10 carbon atoms, the alkyl, alkoxy or alkoxyalkyl group may have a linear, branched or cyclic structure, m represents an integer of 3 to 10, n represents an integer of 1 to 500, and $R^3$, m or n present in plurality within the same molecule may be the same or different, provided that $R^3$ present in plurality within the same molecule are not a hydrogen atom at the same time.

(3) A solid polymer electrolyte which is a polymer of a polymerizable compound having a branched carbonate structure described in (1) or (2) above and a polymerizable functional group represented by the following formula (3) and/or (4):

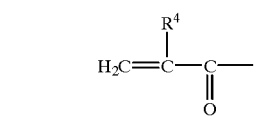
(3)

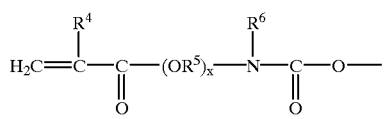
(4)

wherein $R^4$ represents a hydrogen atom or an alkyl group having from 1 to 10 carbon atoms, $R^6$ represents a hydrogen atom, an alkyl group having from 1 to 10 carbon atoms, an alkoxy group having from 1 to 10 carbon atoms or an alkoxyalkyl group having from 1 to 10 carbon atoms, the alkyl, alkoxy or alkoxyalkyl group may have a linear, branched or cyclic structure, $R^5$ represents a divalent group which may contain a heteroatom and may have a linear, branched or cyclic structure, and x represents 0 or 1, provided that $R^4$, $R^5$, $R^6$ or x present in plurality within the same molecule may be the same or different.

(4) The solid polymer electrolyte as described in (3) above, wherein the polymerizable compound has a mass average molecular weight of about 100 to about 3,000.

(5) The solid polymer electrolyte as described in (3) or (4) above, wherein the polymerizable compound is liquid at room temperature and the viscosity thereof is about 5,000 mPa·S (25° C.) or less.

(6) The solid polymer electrolyte as described in any one of (1) to (5) above, which comprises at least one organic solvent.

(7) A polymerizable composition for solid polymer electrolytes, comprising at least one polymerizable compound described in any one of (3), (4) and (5) above and at least one electrolyte salt.

(8) The polymerizable composition for solid polymer electrolytes as described in (7) above, which comprises at least one organic solvent.

(9) The polymerizable composition for solid polymer electrolytes as described in 8) above, wherein the viscosity is about 6.0 mPa·S (25° C.) or less.

(10) A solid polymer electrolyte obtained by polymerizing the polymerizable composition described in (7) above.

(11) A solid polymer electrolyte obtained by polymerizing the polymerizable composition described in (8) above.

(12) A solid polymer electrolyte obtained by polymerizing the polymerizable composition described in (9) above.

(13) The solid polymer electrolyte as described in any one of (1), (2), (10), (11) and (12) above, wherein the electrolyte salt is at least one electrolyte salt selected from an alkali metal salt, a quaternary ammonium salt and a quaternary phosphonium salt.

(14) The polymerizable composition for a solid polymer electrolyte as described in any one of (7), (8) and (9) above, wherein the electrolyte salt is at least one electrolyte salt selected from an alkali metal salt, a quaternary ammonium salt and a quaternary phosphonium salt.

(15) The solid polymer electrolyte as described in any one of (6), (11) and (12) above, wherein the organic solvent is at least one organic solvent selected from carbonates, aliphatic esters, ethers, lactones, sulfoxides and amides.

(16) The polymerizable composition for solid polymer electrolytes as described in (8) or (9) above, wherein the organic solvent is at least one organic solvent selected from carbonates, aliphatic esters, ethers, lactones, sulfoxides and amides.

(17) A battery using a solid polymer electrolyte described in any one of (1) to (6), (10) to (13) and (15) above.

(18) The battery as described in (17) above, which is a lithium primary or lithium secondary battery using, as the electrolyte salt, at least one member selected $LiPF_6$, $LiBF_4$, $LiAsF_6$ and $LiN(A-SO_2)_2$, wherein A represents a perfluoroalkyl group having from 1 to 10 carbon atoms.

(19) An electric double-layer capacitor using a solid polymer electrolyte described in any one of (1) to (6), (10) to (13) and (15) above.

(20) An electrochromic device using a solid polymer electrolyte described in any one of (1) to (6), (10) to (13) and (15) above.

(21) A polymerizable compound represented by formula (5):

$$H_2C=\overset{R^4}{\underset{}{C}}-\underset{\overset{\|}{O}}{C}-O-\left[\left(\underset{\overset{}{R^2}}{\overset{R^1}{\underset{}{C}}}\right)_m-O-\underset{\overset{\|}{O}}{C}-O\right]_n-R^7 \quad (5)$$

wherein $R^1$ and $R^2$ each represents a hydrogen atom, an alkyl group having from 1 to 10 carbon atoms, an alkoxy group having from 1 to 10 carbon atoms or an alkoxyalkyl group having from 1 to 10 carbon atoms, the alkyl, alkoxy or alkoxyalkyl group may have a linear, branched or cyclic structure, m represents an integer of 3 to 10, n represents an integer of 1 to 500, $R^4$ represents hydrogen or an alkyl group having from 1 to 10 carbon atoms, the alkyl group may have a linear, branched or cyclic structure, $R^7$ represents a chained, branched and/or cyclic organic group having from 1 to 30 carbon atoms, which may contain a heteroatom and/or an unsaturated bond, and $R^1$, $R^2$, $R^4$, $R^7$, m or n present in plurality within the same molecule may be the same or different, provided that $R^1$ or $R^2$ present in plurality within the same molecule are not a hydrogen atom at the same time.

(22) A polymerizable compound represented by formula (6):

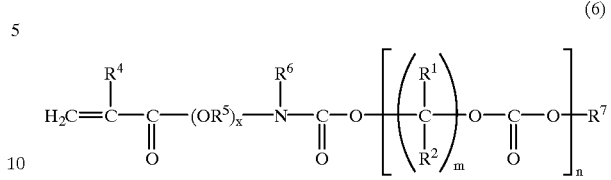

wherein $R^1$ and $R^2$ each represents a hydrogen atom, an alkyl group having from 1 to 10 carbon atoms, an alkoxy group having from 1 to 10 carbon atoms or an alkoxyalkyl group having from 1 to 10 carbon atoms, the alkyl, alkoxy or alkoxyalkyl group may have a linear, branched or cyclic structure, m represents an integer of 3 to 10, n represents an integer of 1 to 500, x represents 0 or 1, $R^4$ represents a hydrogen atom or an alkyl group having from 1 to 10 carbon atoms, the alkyl group may have a linear, branched or cyclic structure, $R^7$ represents a chained, branched and/or cyclic organic group having from 1 to 30 carbon atoms, which may contain a heteroatom and/or an unsaturated bond, $R^6$ represents a hydrogen atom, an alkyl group having from 1 to 10 carbon atoms, an alkoxy group having from 1 to 10 carbon atoms or an alkoxyalkyl group having from 1 to 10 carbon atoms, the alkyl, alkoxy or alkoxyalkyl group may have a linear, branched or cyclic structure, $R^7$ represents a chained, branched and/or cyclic organic group having from 1 to 30 carbon atoms, which may contain a heteroatom and/or an unsaturated bond, and $R^1$, $R^2$, $R^4$, $R^5$, $R^6$, $R^7$, m or n present in plurality within the same molecule may be the same or different, provided that $R^1$ or $R^2$ present in plurality within the same molecule are not a hydrogen atom at the same time.

DESCRIPTION OF THE PRESENT INVENTION

Figure 1:
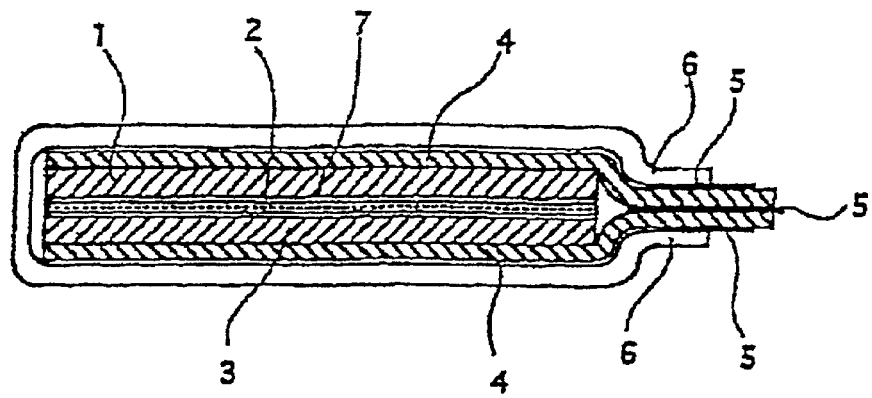
FIG. 1 is a schematic cross-sectional view showing a thin battery according to one embodiment of the battery of the present invention.

The present invention is described in detail below.

(Solid Polymer Electrolyte)

The solid polymer electrolyte of the present invention fundamentally comprises (a) a polymer compound and (b) an electrolyte salt as main constituent components and may further comprise (c) an organic solvent and other additives such as inorganic oxide. Respective components are described in detail below.

(a) Polymer Compound

The polymer compound as a main constituent component of the solid polymer electrolyte of the present invention is electronically non-conducting and can absorb and hold various organic polar solvents. This compound contains a crosslinked and/or side chain group having a branched carbonate structure represented by the following formula (1):

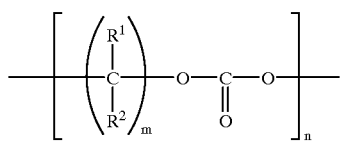

(1)

wherein $R^1$ and $R^2$ each represents a hydrogen atom, an alkyl group having from 1 to 10 carbon atoms, an alkoxy group having from 1 to 10 carbon atoms or an alkoxyalkyl group having from 1 to 10 carbon atoms, the alkyl, alkoxy or alkoxyalkyl group may have a linear, branched or cyclic structure, m represents an integer of 3 to 10, n represents an integer of 1 to 500, and $R^1$, $R^2$, m or n present in plurality within the same molecule may be the same or different, provided that $R^1$ or $R^2$ present in plurality within the same molecule are not a hydrogen atom at the same time.

In the formula above, if m is too large, the relative ratio of the carbonate group in the polymer compound becomes small and this is disadvantageous in that the dielectric constant decreases, the electrolyte salt is difficult to dissociate and the polymer compound is increased in the hydrophobicity and decreased in the compatibility with various polar solvents. If m is excessively small, the flexibility of the polymer decreases and at the time of synthesis, production of cyclic by-products disadvantageously increases. m is preferably from 3 to 8.

When a branched chain is introduced into a polymer compound as in the formula above, the polymer compound is reduced in the crystallinity and in the melting point, glass transition point or viscosity. However, if the number of carbon atoms in $R^1$ or $R^2$ is excessively large, the hydrophobicity of the polymer compound increases and this is disadvantageous in that the dielectric constant decreases, the electrolyte salt is difficult to dissociate and compatibility with various polar solvents decreases. The number of carbon atoms in $R^1$ or $R^2$ is preferably from 1 to 5.

In the polymer used for the solid polymer electrolyte of the present invention, the number n of continuous repetition of the carbonate structure represented by formula (1) is from 1 to 500, preferably 5 to 300.

In another embodiment, the polymer compound for use in the present invention comprises a crosslinked and/or side chain group having a branched carbonate structure represented by formula (2):

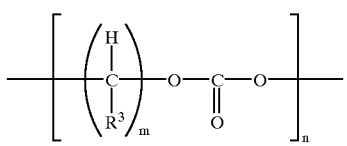

(2)

wherein $R^3$ represents a hydrogen atom, an alkyl group having from 1 to 10 carbon atoms, an alkoxy group having from 1 to 10 carbon atoms or an alkoxyalkyl group having from 1 to 10 carbon atoms, the alkyl, alkoxy or alkoxyalkyl group may have a linear, branched or cyclic structure, m represents an integer of 3 to 10, n represents an integer of 1 to 500, and $R^3$, m or n present in plurality within the same molecule may be the same or different, provided that $R^3$ present in plurality within the same molecule are not a hydrogen atom at the same time.

In the formula above, if m is too large, the relative ratio of the carbonate group in the polymer compound becomes small, which is disadvantageous in that the dielectric constant decreases, the electrolyte salt is difficult to dissociate and the polymer compound is increased in hydrophobicity and decreased in compatibility with various polar solvents. If m is excessively small, the flexibility of the polymer decreases and during synthesis, production of cyclic by-products disadvantageously increases. m is preferably from 3 to 8.

When a branched chain is introduced into a polymer compound as in the formula above, the polymer compound is reduced in crystallinity and in melting point, glass transition point or viscosity. However, if the number of carbon atoms in $R^3$ is excessively large, the hydrophobicity of the polymer compound increases, which is disadvantageous in that the dielectric constant decreases, the electrolyte salt is difficult to dissociate and compatibility with various polar solvents decreases. The number of carbon atoms in $R^3$ is preferably from 1 to 5.

In the polymer used for the solid polymer electrolyte of the present invention, the number n of continuous repetition of the carbonate structure represented by formula (2) is from 1 to 500, preferably 5 to 300.

The polymer for use in the solid polymer electrolyte of the present invention is preferably (A) a polymer obtained by polymerizing at least one polymerizable compound having a carbonate structure represented by formula (1) or (2) and having a polymerizable functional group represented by the following formula (3) and/or (4):

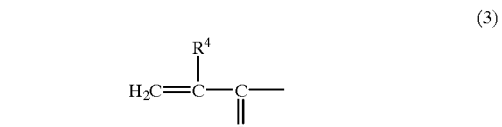

(3)

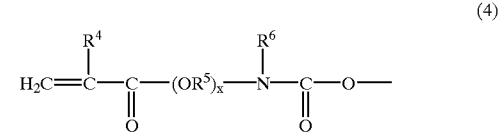

(4)

wherein $R^4$ represents a hydrogen atom or an alkyl group having from 1 to 10 carbon atoms, $R^6$ represents a hydrogen atom, an alkyl group having from 1 to 10 carbon atoms, an alkoxy group having from 1 to 10 carbon atoms or an alkoxyalkyl group having from 1 to 10 carbon atoms, the alkyl, alkoxy or alkoxyalkyl group may have a linear, branched or cyclic structure, $R^5$ represents a divalent group which may contain a heteroatom and may have a linear, branched or cyclic structure, and x represents 0 or 1, provided that $R^4$, $R^5$, $R^6$ or x present in plurality within the same molecule may be the same or different, because the obtained solid polymer electrolyte is facilitated in processing or in compounding with an electrode used for various electrochemical devices.

A polymer obtained by polymerizing a compound having one functional group represented by formula (3) and/or (4) has no crosslinked structure and is deficient in the film strength. Therefore, when this polymer is formed into a thin film, short circuit may occur. Accordingly, the polymer is preferably crosslinked by copolymerizing with a polyfunctional polymerizable compound having two or more functional groups represented by formula (3) and/or (4), or preferably used in combination with a polymer obtained from a polyfunctional polymerizable compound having two or more functional groups represented by formula (3) and/or (4). However, in the case where low viscosity is intended, a low molecular weight form of a monofunctional polymerizable compound having one functional group is preferably used in an amount as large as possible, because the crosslinking density does not increase after the polymerization and low viscosity can be attained. The amount of the monofunctional polymerizable compound mixed varies depending on the molecular weight or structure and cannot be indiscriminately limited, however, it is preferably from 20 to 90% by mass, more preferably from 40 to 85% by mass, based on all polymerizable compounds.

Also, the polymer for use in the solid polymer electrolyte of the present invention may be (B) a copolymer obtained by copolymerizing at least one polymerizable compound having a polymerizable functional group represented by formula (3) and/or (4) and at least one polymerizable compound having a functional group copolymerizable with the above-described polymerizable compound and a carbonate structure represented by formula (1), or (C) a mixture of at least one polymer compound having a carbonate structure represented by formula (1) and a polymer obtained by polymerizing at least one polymerizable compound having a polymerizable functional group represented by formula (3) and/or (4).

The polymerizable compound for use in the solid polymer electrolyte of the present invention is preferably liquid at room temperature and low in viscosity in view of processability when forming a solid polymer electrolyte by polymerizing the polymerizable compound or a polymerizable composition resulting from mixing with an electrolyte salt or the like, or in view of impregnating ability when performing the polymerization by injecting the compound or composition into an electrochemical device. The viscosity at 25° C. of the polymerizable compound for use in the solid polymer electrolyte of the present invention is preferably about 10,000 mPa·s or less, more preferably about 5,000 mPa·s.

The polymerizable compound for use in the solid polymer electrolyte of the present invention preferably has a molecular weight as small as possible to have a low viscosity. However, if the molecular weight is excessively small, the crosslinking density or crystallinity increases after the polymerization, which is disadvantageous in that the solid polymer electrolyte is reduced in temperature characteristics of ionic conductivity or in contacting property with various electrochemical device materials. The viscosity is affected not only by the molecular weight, but also by the structure such as branched chain. Therefore, the molecular weight of the polymerizable compound for use in the solid polymer electrolyte of the present invention is preferably from about 100 to about 3,000, more preferably from about 150 to about 1,500.

Specific examples of the polymerizable compound (A) include the compounds represented by the following formulae (5) and (6):

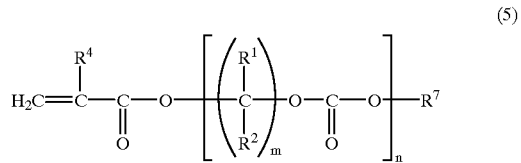
(5)

wherein $R^1$ and $R^2$ each represents a hydrogen atom, an alkyl group having from 1 to 10 carbon atoms, an alkoxy group having from 1 to 10 carbon atoms or an alkoxyalkyl group having from 1 to 10 carbon atoms, the alkyl, alkoxy or alkoxyalkyl group may have a linear, branched or cyclic structure, m represents an integer of 3 to 10, n represents an integer of 1 to 500, $R^4$ represents hydrogen or an alkyl group having from 1 to 10 carbon atoms, the alkyl group may have a linear, branched or cyclic structure, $R^7$ represents a chained, branched and/or cyclic organic group having from 1 to 30 carbon atoms, which may contain a heteroatom and/or an unsaturated bond, and $R^1$, $R^2$, $R^4$, $R^7$, m or n present in plurality within the same molecule may be the same or different, provided that $R^1$ or $R^2$ present in plurality within the same molecule are not a hydrogen atom at the same time.

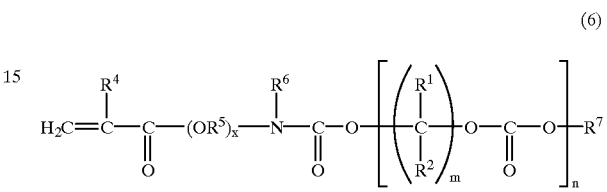
(6)

wherein $R^1$ and $R^2$ each represents a hydrogen atom, an alkyl group having from 1 to 10 carbon atoms, an alkoxy group having from 1 to 10 carbon atoms or an alkoxyalkyl group having from 1 to 10 carbon atoms, the alkyl, alkoxy or alkoxyalkyl group may have a linear, branched or cyclic structure, m represents an integer of 3 to 10, n represents an integer of 1 to 500, x represents 0 or 1, $R^4$ represents a hydrogen atom or an alkyl group having from 1 to 10 carbon atoms, the alkyl group may have a linear, branched or cyclic structure, $R^7$ represents a chained, branched and/or cyclic organic group having from 1 to 30 carbon atoms, which may contain a heteroatom and/or an unsaturated bond, $R^6$ represents a hydrogen atom, an alkyl group having from 1 to 10 carbon atoms, an alkoxy group having from 1 to 10 carbon atoms or an alkoxyalkyl group having from 1 to 10 carbon atoms, the alkyl, alkoxy or alkoxyalkyl group may have a linear, branched or cyclic structure, $R^7$ represents a chained, branched and/or cyclic organic group having from 1 to 30 carbon atoms, which may contain a heteroatom and/or an unsaturated bond, and $R^1$, $R^2$, $R^4$, $R^5$, $R^6$, $R^7$, m or n present in plurality within the same molecule may be the same or different, provided that $R^1$ or $R^2$ present in plurality within the same molecule are not a hydrogen atom at the same time.

The method for synthesizing the polymerizable compound having a carbonate structure represented by formula (1) and a polymerizable functional group represented by formula (3) is not particularly limited and the polymerizable compound can be easily obtained, for example, by dehydration-condensing an acid having a polymerizable functional group, such as acroyl acid, and a carbonate-ol having a hydroxyl group at the terminal, in the presence of an acid catalyst or the like as shown below.

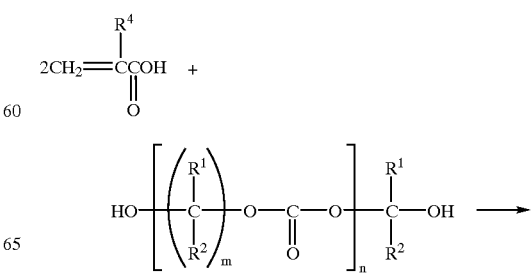

-continued

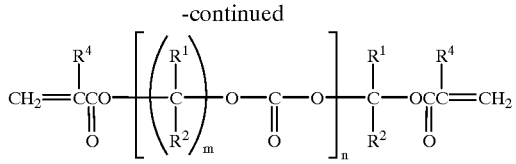

wherein $R^1$, $R^2$, $R^4$, m and n have the same meanings as in formula (5).

The method for synthesizing the polymerizable compound having a carbonate structure represented by formula (1) and a polymerizable functional group represented by formula (4) is not particularly limited and the polymerizable compound can be easily obtained, for example, by reacting an acryloyl-based isocyanate compound represented by the formula:

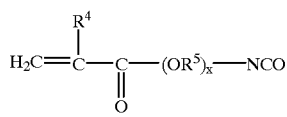

with a carbonate-ol having a hydroxyl group at the terminal, in the presence of a urethanization reaction catalyst as shown below.

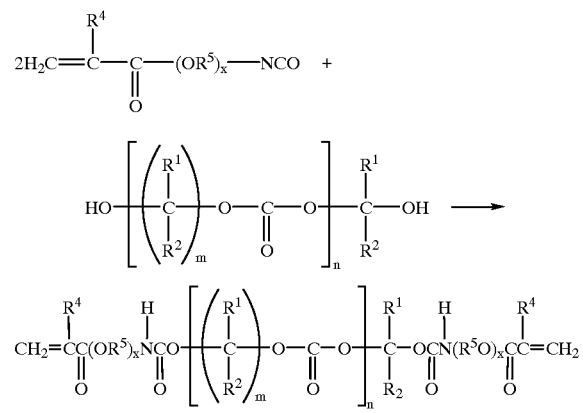

wherein $R^1$, $R^2$, $R^4$, $R^5$, n, m and x have the same meanings as in formula (6).

The polymer compound obtained by polymerizing a compound having a polymerizable functional group represented by formula (4) contains a urethane group, which is advantageous in that the dielectric constant is high and the solid polymer electrolyte obtained is increased in ionic conductivity. Furthermore, the compound having a polymerizable functional group represented by (4) has good polymerizability, and when the compound is formed into a thin film, the film advantageously has a sufficiently high film strength and a large capacity for including an electrolytic solution.

The polymerizable compound having a carbonate structure represented by formula (1) and, at the same time, having a polymerizable functional group represented by formula (3) and/or (4), which is suitable for obtaining the polymer for use in the solid polymer electrolyte of the present invention, is polymerized in the presence of a polymerization initiator to form a solid polymer electrolyte. These polymerizable compounds can be used individually or in combination of two or more thereof. Also, at least one of these polymerizable compounds may be copolymerized with another polymerizable compound.

Another polymerizable compound copolymerizable with the polymerizable compound having a carbonate structure represented by formula (1) and a polymerizable functional group represented by formula (3) and/or (4) is not particularly limited and examples thereof include (meth)acrylic acid alkyl esters such as methyl methacrylate and n-butyl acrylate; various urethane acrylates; (meth)acrylamide-based compounds such as acrylamide, methacrylamide, N,N-dimethylacrylamide, N,N-dimethyllmethacrylamide, vinylene carbonate, (meth)acryloyl carbonate, N-vinylpyrrolidone, acryloylmorpholine, methacryloylmorpholine, N,N-dimethylaminopropyl (meth) acrylamide; styrene-based compounds such as styrene and α-methylstyrene; N-vinylamide-based compounds such as N-vinylacetamide and N-vinylformamide; and alkyl vinyl ethers such as ethyl vinyl ether. Among these, preferred are (meth)acrylic acid esters and urethane (meth)acrylates.

The polymer for use in the solid polymer electrolyte of the present invention may be a polymer obtained from at least one polymerizable compound having a carbonate structure represented by formula (1) and a polymerizable functional group represented by formula (3) and/or (4), and/or a mixture of a copolymer using the above-described polymerizable compound as a copolymerization component with another polymer, examples of which include polyethylene oxides, polypropylene oxides, polyacrylonitrile, poly(meth) acrylic acid esters, polystyrene, polyphosphagene and polymers such as polysiloxane, polysilane, polyvinylidene fluoride and polytetrafluoroethylene.

The amount of the structural unit derived from the polymer having a carbonate structure represented by formula (1) varies depending on whether the polymerizable compound having a carbonate structure represented by formula (1) and, at the same time, having a polymerizable functional group represented by formula (3) and/or (4) is homopolymerized, copolymerized with another copolymerization component or mixed with another polymer, and thus cannot be indiscriminately specified. However, in view of ionic conductivity, film strength, heat resistance and current characteristics of the solid polymer electrolyte obtained, the content thereof is preferably 50% by mass or more, more preferably 70% by mass or more, based on the total amount of the polymer components.

The polymerization of the polymerizable compound having a carbonate structure represented by formula (1) and a polymerizable functional group represented by formula (3) and/or (4) may be performed by a general method using the polymerizability of acryloyl or methacryloyl group as the functional group. More specifically, the polymerizable compound alone or a mixture of the polymerizable compound and another polymerizable compound copolymerizable therewith may be subjected to radical polymerization, cationic polymerization or anionic polymerization using a radical polymerization catalyst such as 2,2'-azobisisobutyronitrile (AIBN) and benzoyl peroxide (BPO), a cationic polymerization catalyst such as protonic acid (e.g., $CF_3COOH$) and Lewis acid (e.g., $BF_3$, $AlCl_3$), or an anionic polymerization catalyst such as butyl lithium, sodium naphthalene and lithium alkoxide. Furthermore, the polymerizable compound or polymerizable mixture may also be polymerized after forming it into a film or the like or after injecting or impregnating it into various electrode materials.

(b) Electrolyte Salt

The kind of electrolyte salt used in the present invention is not particularly limited and any electrolyte may be used as long as it contains an ion intended to be used as a charge carrier. The electrolyte salt preferably has a large dissociation constant in a solid polymer electrolyte, and examples thereof include alkali metal salts of trifluoromethanesulfonic acid, such as $LiCF_3SO_3$, $NaCF_3SO_3$ and $KCF_3SO_3$, alkali metal salts of perfluoroalkanesulfonic imide, such as $LiN(CF_3SO_2)_2$ and $LiN(CF_3CF_2SO_2)_2$, alkali metal salts of hexafluorophosphoric acid, such as $LiPF_6$, $NaPF_6$ and $KPF_6$, perchlorate alkali metal salts such as $LiCl_4$ and $NaClO_4$, tetrafluoroborates such as $LiBF_4$ and $NaBF_4$, and alkali metal salts such as $LiSCN$, $LiAsF_6$, $LiI$, $NaI$, $NaAsF_6$ and $KI$. Examples of the ammonium salt include quaternary ammonium salts of perchloric acid, such as tetraethylammonium perchlorate, quaternary ammonium salts of tetrafluoroboric acid, such as $(C_2H_5)_4NBF_4$, quaternary ammonium salts such as $(C_2H)_4NPF_6$, and quaternary phosphonium salts such as $(CH_3)_4P.BF_4$ and $(C_2H)_4P.BF_4$. Among these electrolytes, in view of solubility in an organic solvent and ionic conductivity, $LiPF_6$, $LiBF_4$, $LiAsF_6$ and alkali metal salts and quaternary ammonium salts of perfluoroalkanesulfonic imide are preferred.

The ratio between the polymer component and the electrolyte salt compounded in the solid polymer electrolyte of the present invention is preferably such that the electrolyte salt is from 0.1 to 50% by mass, more preferably from 1 to 30% by mass, based on the weight of polymer. If the electrolyte compounded is present in a proportion of 50% by mass or more, the ion transfer is greatly inhibited, whereas if the proportion thereof is less than 0.1% by mass, the absolute amount of ion is deficient and ionic conductivity is low.

(c) Organic Solvent

The solid polymer electrolyte of the present invention preferably contains an organic solvent because ionic conductivity of the solid polymer electrolyte is further improved. The organic solvent which can be used is suitably a compound having good compatibility with the polymer having a carbonate structure represented by formula (1) used in the solid polymer electrolyte of the present invention, having a large dielectric constant, ensuring high solubility of the electrolyte salt (b), having a boiling point of 60° C. or more and being wide in an electrochemical stability range. An organic solvent (non-aqueous organic solvent) having a low water content is more preferred.

Examples of such a solvent include ethers such as 1,2-diethoxyethane, 2-methyltetrahydrofuran, crown ether, triethylene glycol methyl ether and tetraethylene glycol dimethyl ether; carbonic esters such as ethylene carbonate, propylene carbonate, dimethyl carbonate, diethyl carbonate, methyl ethyl carbonate and vinylene carbonate; aliphatic esters such as methyl propionate and methyl formate; aromatic nitriles such as benzonitrile and tolunitrile; amides such as dimethylformamide; sulfoxides such as dimethylsulfoxide; lactones such as γ-butyrolactone; sulfur compounds such as sulfolane; N-methylpyrrolidone, N-vinylpyrrolidone and phosphoric esters. Among these, carbonic esters, aliphatic esters and ethers are preferred, and carbonates are more preferred. These solvents may be used individually or may be used as a mixed solvent by mixing two or more thereof.

As the amount of the organic solvent added is larger, the solid polymer electrolyte obtained is further improved in ionic conductivity. Accordingly, the organic solvent content is generally large, however, curability, film forming property, or liquid holding property or mechanical strength of the solid polymer electrolyte may be impaired if the content is excessively large. The content is preferably from 2 to 20 times, more preferably from 3 to 12 times, the mass of the polymer used for the solid polymer electrolyte of the present invention.

(d) Inorganic Oxide

In the foregoing, the primary components of the solid polymer electrolyte of the present invention were described one by one, and as long as the objects of the present invention are not inhibited, other additives may also be added.

For example, the electrolyte may be used as a composite electrolyte having added thereto inorganic oxide fine particle of various types. By using the electrolyte as such, not only strength and film uniformity are improved, but ionic conductivity and mobility can also be increased without impairing the effect of improving strength, because fine holes are generated between the inorganic oxide and the polymer. In particular, when a solvent is added, a free electrolytic solution disperses into the holes, namely, within the composite electrolyte.

For the inorganic oxide fine particle, those which are electronically non-conducting and electrochemically stable are selected. Particularly, those having ionic conductivity are preferred. Specific examples thereof include ion-conductive or electronically non-conducting ceramic fine particles such as α-,β-or γ-alumina, silica, titania, magnesia and hydrotalcite.

For the purpose of increasing the amount of electrolyte-containing solution held in the solid polymer electrolyte and increasing ionic conductivity and mobility, the inorganic oxide fine particle preferably has a specific surface area as large as possible. The specific surface area by BET method is preferably about 5 $m^2/g$ or more, more preferably about 50 $m^2/g$ or more. The crystal grain size of the inorganic oxide fine particle is not particularly limited insofar as it can be mixed with a polymerizable composition, however, the size (average crystal grain size) is preferably from 0.01 to 20 $\mu m$, more preferably from 0.01 to 2 $\mu m$.

The inorganic fine particle used may have various shapes such as spherical, egg-like, cubic, rectangular, cylindrical and bar-like forms.

If the amount of the inorganic fine particle added is excessively large, the solid polymer electrolyte is disadvantageously reduced in strength or ionic conductivity, or becomes difficult of film formation. Accordingly, the amount of the inorganic fine particle added is preferably 50% by mass or less, more preferably from 0.1 to 30% by mass, based on the solid polymer electrolyte.

(Production Process of Solid Polymer Electrolyte)

The solid polymer electrolyte of the present invention can be produced by forming a polymer obtained from at least one polymerizable compound described above or a copolymer using the polymerizable compound as a copolymerization component into a film, polymerizing the film and contacting it with an electrolyte salt dissolved in an organic solvent, or by preparing a polymerizable composition comprising the polymerizable compound and other components, molding the composition, for example, into a film and polymerizing the film.

Specifically, in the latter method, at least one polymerizable compound and at least one electrolyte salt such as alkali metal salt, quaternary ammonium salt, quaternary phosphonium salt and transition metal salt, are mixed and after adding and mixing another polymerizable compound, a plasticizer, an organic solvent and/or an inorganic oxide, if desired, to prepare a polymerizable composition, the composition is formed into a film and polymerized under heating and/or irradiation of active rays in the presence or absence of an initiator described above, whereby a solid polymer electrolyte of the present invention is obtained. According to this method, the latitude of processing is broadened, which is greatly advantageous in the application.

The conditions preferred for the curing of the polymerizable composition may be determined by selecting a thermopolymerization initiator according to the desired molding temperature, the kind and curability of the polymerizable compound, and the boiling point of solvent, and considering the temperature necessary for halving the active oxygen amount in the initiator (half-life temperature). The curing temperature and the curing rate may be determined based on the half-life and activation energy of the thermopolymerization initiator. For example, the temperature necessary for the half-life of 10 hours is from room temperature to 100° C., preferably from 40° C. to 70° C.

In the case of polymerization under irradiation of active rays, although it may vary depending on the kind of the polymerizable compound, the polymerization may be performed, for example, by irradiating ultraviolet ray of several mW or more using an initiator, such as benzyl methyl ketal and benzophenone, or by irradiating γ ray, electron beam or the like using a solvent. The solvent may be any solvent as long as it does not inhibit the polymerization.

The solid polymer electrolyte of the present invention may also be used as a composite electrolyte by compounding it with, for example, a porous polymer film of various types to improve strength, to form uniform film or to prevent short circuit between electrodes. In this case, the separator, after the absorption of electrolytic solution may be reduced in ionic conductivity or deteriorated in the stability depending on the kind of the polymer used, the film shape or the compounding ratio. Therefore, the film compounded must be appropriately selected. Examples of the film compounded include a porous polyolefin sheet, such as polypropylene non-woven fabric and network polyolefin sheet (e.g., polyethylene-made net), polyolefin-made microporous film, such as CELLGUARD (trade name), nylon non-woven fabric, glass fiber and ceramic fiber. Among these, porous polyolefin film is preferred.

The porous polymer film compounded may be sufficient if it has a porosity on the order of 10 to 95% and a thickness on the order of 1 to 200 μm, however, the porosity is preferably large as much as possible insofar as the strength is not impaired. The porosity is preferably from about 40 to about 95% and the thickness is preferably from about 5 to about 50 μm.

The compounding method is not particularly limited, however, for example, a polymerizable composition obtained by adding and mixing at least one polymerizable compound described above or additionally at least one electrolyte salt and depending on the case, other components, is impregnated into a porous polymer film and the (meth)acryloyl-based compound is polymerized, whereby uniform compounding can be attained and the film thickness can be easily and simply controlled.

The use of the solid polymer electrolyte of the present invention is described in greater detail below by referring to a battery, an electric double-layer capacitor and an electrochromic device.

(Battery and Production Process Thereof)

FIG. 1 is a schematic cross sectional view showing an example of a thin-film solid battery, which is a battery according to the present invention. In the FIG. 1, 1 is positive electrode, 2 is porous separator, 3 is negative electrode, 4 is collector, 5 is heat fusion polymer film, 6 is a device case and 7 is a solid polymer electrolyte.

In the construction of the battery according to the present invention, when an electroactive substance (positive electroactive substance) having a high oxidation-reduction potential, such as metal oxide, metal sulfide, electrically conducting polymer or carbon material, is used for the positive electrode 1, a battery having high voltage and high capacity can be obtained. Among these electroactive substances, metal oxides, such as cobalt oxide, manganese oxide, vanadium oxide, nickel oxide and molybdenum oxide, and metal sulfides, such as molybdenum sulfide, titanium sulfide and vanadium sulfide, are preferred because the filling density and volume capacity density can be increased. In view of high capacity and high voltage, manganese oxide, nickel oxide and cobalt oxide are more preferred.

The method for producing the metal oxide or metal sulfide is not particularly limited and they may be produced by a general electrolytic method or heating method described, for example, in *Denki Kagaku* (*Electrochemistry*), Vol. 22, page 574 (1954). In the case of a lithium battery, the electroactive substance is preferably used in such a state that a Li element is intercalated (compounded) in the metal oxide or metal sulfide, for example, in the form of $Li_xCoO_2$ and $Li_xMn_2O_4$. The method for intercalating the Li element is not particularly limited and, for example, a method of electrochemically intercalating a Li ion or a method described in U.S. Pat. No. 4,357,215, where a salt such as $Li_2CO_3$ is mixed with a metal oxide and then heat-treated, may be used.

In view of easy formation of a flexible and thin film, an electrically conducting polymer is preferred. Examples of the electrically conducting polymer include polyaniline, polyacetylene and derivatives thereof, poly-p-phenylene and derivatives thereof, polypyrrole and derivatives thereof, polythienylene and derivatives thereof, polypyridinediyl and derivatives thereof, polyisothianaphthenylene and derivatives thereof, polyfurylene and derivatives thereof, polyselenophene and derivatives thereof, and polyarylene vinylene and derivatives thereof, such as poly-p-phenylene vinylene, polythienylene vinylene, polyfurylene vinylene, polynaphthenylene vinylene, polyselenophene vinylene and polypyridinediyl vinylene. Among these, preferred are organic solvent-soluble polymers of aniline derivatives.

Examples of the carbon material include natural graphite, artificial graphite, vapor grown graphite, petroleum coke, coal coke, pitch-type carbon, polyacene, and furalene such as C60 and C70.

The negative electroactive substance used for the negative electrode 3 of the battery according to the present invention is preferably a substance having a low oxidation-reduction potential, and the above-described alkali metal ion is used as the carrier, such as alkali metal, alkali metal alloy, carbon material, metal oxide and metal chalcogenide to attain a high-voltage and high-capacity battery. Among these negative electroactive substances, lithium metals and lithium alloys, such as lithium/aluminum metal, lithium/lead alloy and lithium/antimony alloy, are more preferred in view of their lowest oxidation-reduction potential. In addition, carbon materials having occluded thereinto lithium ion are also preferred because a low oxidation-reduction potential is exhibited and they are stable and safe. Examples of the material capable of occluding or releasing lithium ion include inorganic compounds such as tin oxide, natural graphite, artificial graphite, vapor grown graphite, petroleum coke, coal coke, pitch-type carbon, polyacene, and furalene such as C60 and C70.

For the collector 4, a material having electronic conduction, electrochemical corrosion resistance and a surface area as large as possible is preferably used. Examples thereof include various metals and sintered body thereof, electronically conducting polymers and carbon sheet.

An example of a production process of a battery according to the present invention is described below.

A positive electrode 1 and a negative electrode 3 formed on a collector so that they do not come into contact with each other by interposing a porous separator 2 therebetween are placed in an aluminum laminate-made device case 6. Then, a polymerizable composition, which becomes the solid polymer electrolyte of the present invention and in which a thermopolymerization initiator is added, injected and impregnated. Thereafter, the opening is sealed through a heat fusion polymer film 5 and the polymerizable composition within the battery is cured by heating. As a result, a thin solid battery shown in FIG. 1 is obtained, where a positive electrode 1, a negative electrode 3, a separator 2 and a solid polymer electrolyte 7 are uniformly adhered. The device case is not limited to the aluminum laminate but a metal such as SUS (stainless steel), a resin such as polypropylene, a ceramic such as insulating glass, or the like may also be used according to the end use without any particular limitation. The device case may have any shape, such as cylinder, box or sheet.

The battery containing the solid polymer electrolyte of the present invention may also be produced by a method of impregnating the polymerizable composition into a positive electrode 1 and/or a negative electrode 3, curing the composition, coating further the polymerizable composition on either one electrode to have a uniform thickness, and curing it by the above-described method to form a solid polymer electrolyte film 7 on the electrode. Thereafter, another electrode is attached to the thus-formed solid polymer electrolyte film layer, which is placed in an aluminum laminate-made device case 6, and the opening is sealed through a heat fusion polymer film 5, whereby a thin solid battery shown in FIG. 1 is obtained. In this case, if the solid polymer electrolyte film formed on the electrode has no problem in mechanical strength, a porous separator is not necessary.

(Electric Double-Layer Capacitor and Production Process Thereof)

The electric double-layer capacitor of the present invention is described below.

According to the present invention, an electric double-layer capacitor having high output voltage and large takeout current, and excellent in processability, life and reliability is provided by using the solid polymer electrolyte of the present invention.

Figure 2:
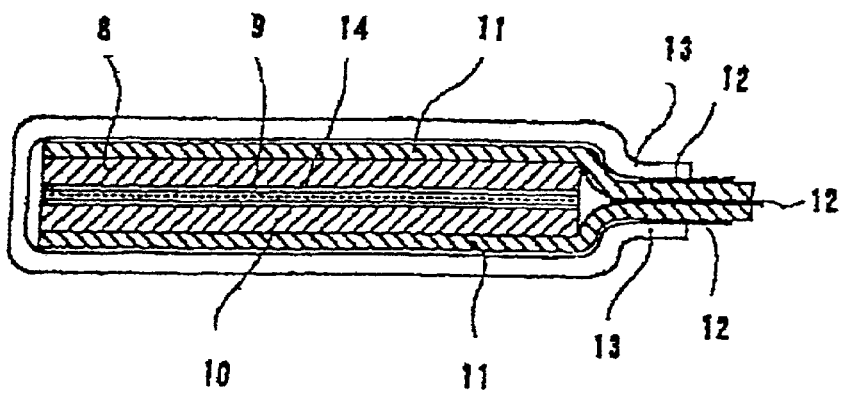
FIG. 2 is a schematic cross-sectional view showing one embodiment of a solid electric double-layer capacitor of the present invention.

FIG. 2 is a schematic cross-sectional view showing an example of an electric double-layer capacitor according to the present invention. A thin cell having a size of about 1 cm×about 1 cm and a thickness of about 0.5 mm, where 11 is a collector, a pair of polarizable electrodes 8 and 10 are disposed in the inner side of the collector, and a porous separator 9 compounded with a solid polymer electrolyte film 14 of the present invention is disposed therebetween. The numeral 13 is a device case and 12 is a heat fusion polymer film.

The polarizable electrodes 8 and 10 are not particularly limited as long as they are an electrode comprising a polarizable material such as carbon material. The polarizable electrodes preferably have a larger specific surface area, because the electric double layer can have a larger capacity. Examples of the material include carbon black materials such as furnace black, thermal black (including acetylene black) and channel black, active carbon materials such as coco shell carbon, natural graphite, artificial graphite, so-called pyrolytic graphite produced by the vapor phase method, polyacene, C60 and C70.

For the collector 11, a material having electronic conduction, electrochemical corrosion resistance and a specific surface area as large as possible is preferably used. Examples thereof include various metals and sintered body thereof, electronically conducting polymers and carbon sheet.

With respect to the shape of the electric double-layer capacitor, other than the sheet form shown in FIG. 2, a coin form or a cylindrical form may be used. The cylindrical electric double-layer capacitor is produced by rolling up a sheet laminate of polarizable electrodes and a solid polymer electrolyte into a cylindrical form, placing the roll in a cylindrical tubular structure body for constructing a capacitor, and sealing it.

The kind of electrolyte salt used in the electric double-layer capacitor of the present invention is not particularly limited and a compound containing an ion intended to serve as a charge carrier may be used. However, those containing an ion capable of exhibiting a large dissociation constant in the solid polymer electrolyte and readily forming an electric double layer with the polarizable electrodes are preferred. Examples of such a compound include quaternary ammonium salts such as $(CH_3)_4NBF_4$ and $(CH_3CH_2)_4NClO_4$, transition metal salts such as $AgClO_4$, quaternary phosphonium salts such as $(CH_3)_4PBF_4$, alkali metal salts such as $LiCF_3SO_3$, $LiPF_6$, $LiI$, $LiBF_4$, $LiSCN$, $LiAsF_6$, $Li(CF_3SO_2)_2$, $NaCF_3SO_3$, $NaPF_6$, $NaClO_4$, $NaI$, $NaBF_4$, $NaAsF_6$, $KCF_3SO_3$, $KPF_6$ and $KI$, organic acids and salts thereof such as p-toluenesulfonic acid, and inorganic acids such as hydrochloric acid and sulfuric acid. Among these, from the standpoint that high output voltage can be taken out and the dissociation constant is large, quaternary ammonium salts, quaternary phosphonium salts and alkali metal salts are preferred. Among quaternary ammonium salts, those where the substituents on nitrogen of the ammonium ion are different, such as $(CH_3CH_2)(CH_3CH_2CH_2CH_2)_3NBF_4$, are preferred because solubility or dissociation constant in the solid polymer electrolyte is large.

An example of a production process of an electric double-layer capacitor according to the present invention is described below.

Polarizable electrode sheets 8 and 10 coated and formed on two collectors are placed in an aluminum laminate-made device case 13 so that they do not come into contact with each other by interposing a porous separator 9 therebetween. Thereafter, a polymerizable composition, which becomes the solid polymer electrolyte of the present invention and in which a thermopolymerization initiator is added, is injected and impregnated. After sealing the opening though a heat fusion polymer film 12, the polymerizable composition within the battery is cured by heating to obtain a thin solid electric double-layer capacitor shown in FIG. 2, where polarizable electrodes 8 and 10, a porous separator 9 and a solid polymer electrolyte 14 are uniformly adhered. The device case is not limited to the aluminum laminate but a metal such as SUS, a resin such as polypropylene, a ceramic such as insulating glass, or the like may also be used according to the end use without any particular limitation.

(Electrochromic Device (ECD) and Production Process Thereof)

Figure 3:
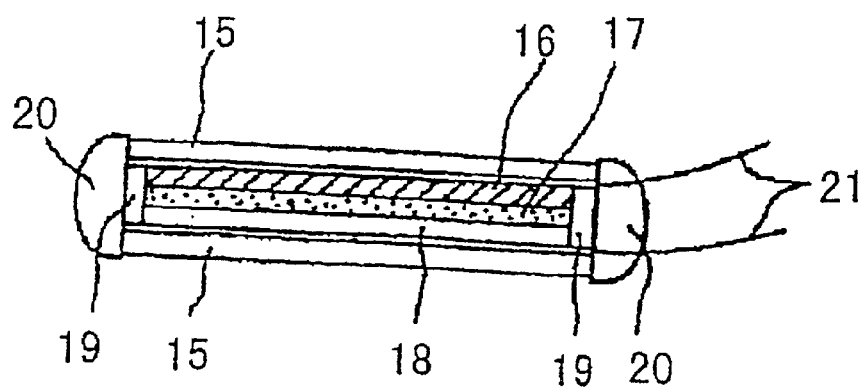
FIG. 3 is a schematic cross-sectional view showing one embodiment of a solid thin ECD of the present invention.

FIG. 3 is a cross-sectional view of a thin film solid ECD having an area of 1.5×1.5 cm, which is an example of ECD of the present invention. In the figure, 15 is a transparent electrically conducting electrode, an electrochromic (EC) layer 16 is formed thereon, and a solid polymer electrolyte film 17 is disposed further thereon. The numeral 18 is a counter electrode, 19 is an insulating film spacer, 20 is an insulating resin sealant and 21 is a lead wire.

In the construction of ECD of the present invention, the EC layer 16 is sufficient if color change can reversibly take place by oxidation and reduction. Representative examples thereof include metal oxides such as tungsten oxide, metal sulfides, viologen derivatives and polymers thereof, and electrically conducting polymers such as polyaniline, polypyrrole, polythiophene and polyisothianaphthene.

The transparent electrically conducting electrode 15 preferably has high electronic conductance, electrochemical corrosion resistance and, if possible, flexibility. For this electrode, a metal such as gold, an electrically conducting oxide such as indium oxide, or an electrically conducting polymer formed into a thin film or compounded on a transparent polymer such as polycarbonate, polymethacrylate and polyethylene terephthalate, or on a glass sheet is used.

The counter electrode preferably has capability of reversibly taking in or out the ion along the movement of ion of the EC layer and has a pale color to clearly show the color change of the EC layer. The material therefor varies depending on the combination with the EC layer and is not particularly limited, but examples thereof include intercalation compounds such as metal oxide and metal sulfide, electrically conducting polymers, hydrogen-storing alloys, and alkali metals or alloys thereof.

A production process of ECD of the present invention is described below.

An EC layer 16 and a counter electrode 18 are laminated so as not to come into contact with each other using an insulating film spacer 19 having a thickness as small as possible and disposed at the edge part of the electrode. Subsequently, a polymerizable composition, which becomes the solid polymer electrolyte of the present invention and in which a thermopolymerization initiator is added, is injected and impregnated therebetween. After sealing the opening with an insulting resin sealant 20, the polymerizable composition within the ECD is cured by heating to obtain a solid ECD shown in FIG. 3, where an EC layer 16, a solid polymer electrolyte 17 and a counter electrode 18 are uniformly adhered.

The viscosity can be determined using a rotary viscometer in accordance with the method described in JIS K7117 and can be measured at various shear rates by changing the rotating speed of the rotary viscometer. The change of viscosity with the passing of time can also be traced by continuously measuring the viscosity for a long period of time at a constant rotational frequency.

The measurement apparatus used is a B-Type viscometer manufactured by Tokimeck, which is corrected with a viscometer-correction standard solution in accordance with JIS Z 8809. The measurement is performed at 25° C. in an argon atmosphere.

EXAMPLES

The present invention is described in greater detail below by referring to the representative Examples, however, these are set forth merely for the purpose of illustration and the present invention should not be construed as being limited thereto. Unless indicated otherwise herein, all parts, percents, ratios and the like are by mass.

Example 1

Synthesis of Polymerizable Compound (Compound 2)

Carbonate-diol (produced by Nippon Polyurethane, mass average molecular weight: 500) (Compound 1) and methacrylate having an isocyanate group (produced by Showa Denko K.K.) (MI) were reacted according to the reaction formula shown below and a polymerizable compound (Compound 2) was obtained through the following procedure.

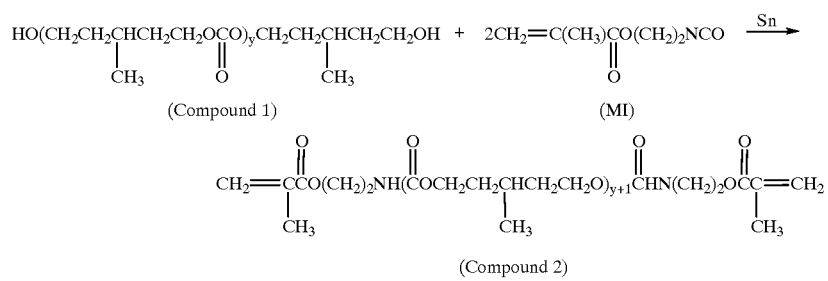

Specifically, 50.0 g of dehydrated Compound 1 (mass average molecular weight: 500, hydroxyl group value: 224 KOHmg/g, water content: 30 ppm) and 32.0 g of MI were reacted in dry air at 50° C. for about 5 hours while adding 0.1 g of dibutyltin dilaurate, and as a result, a colorless viscous liquid was obtained. It was found from $^1$H-NMR and $^{13}$C-NMR that Compound 1 and MI were reacted at 1:2, and since the absorption of isocyanate group of Compound 1 disappeared from the infrared absorption spectrum, a urethane bond was produced, and thus revealing the production of Compound 2. The mass average molecular weight of Compound 2, determined by gel permeation chromatography (GPC), was 800 and the viscosity at 25° C. was 7,000 mPa·s.

Example 2

Synthesis of Polymerizable Compound (Compound 3)

Compound 1 and commercially available methacrylic acid (MA) were reacted according to the reaction formula shown below and a polymerizable compound (Compound 3) was obtained through the following procedure.

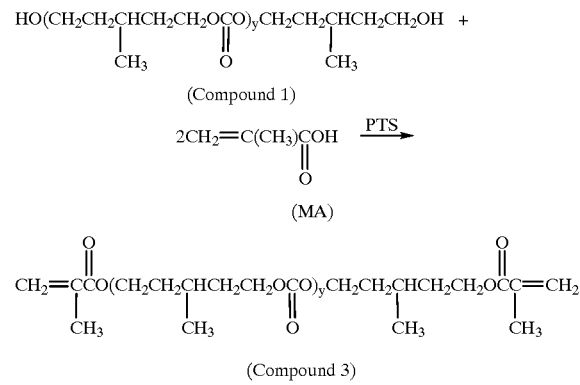

Specifically, 50.0 g of Compound 1 and 20.0 g of MA were reacted in benzene at 90° C. for about 10 hours while adding thereto 2.2 g of p-toluenesulfonic acid (PTS). Thereafter, the reaction solution was neutralized with an aqueous NaOH solution and then subjected to water washing and dehydration. As a result, a colorless viscous liquid was obtained. It was found from $^1$H-NMR and $^{13}$C-NMR that Compound 1 and MA were reacted at 1:2 to produce Compound 3.

The mass average molecular weight of this compound, determined by GPC, was 650 and the viscosity at 25° C. was 230 mPa·s.

Example 3

Synthesis of Polymerizable Compound Mixture (Mixture of Compound 5 and Compound 6)

A mixture of Compound 1 and Compound 4 (1:1 by mol) and a commercially available acrylic acid (AA) were reacted according to the reaction formula shown below and a polymerizable compound (a mixture of Compound 5 and Compound 6) was obtained through the following procedure.

Specifically, 50.0 g of a 1:1 (by mol) mixture (mass average molecular weight: 500, hydroxyl group value: 180 KOHmg/g) of Compound 1 and Compound 4 and 12.0 g of AA were reacted in benzene at 90° C. for about 10 hours while adding thereto 1.5 g of PTS. Thereafter, the reaction solution was neutralized with an aqueous NaOH solution and then subjected to water washing and dehydration. As a result, a colorless viscous liquid was obtained. It was found from $^1$H-NMR and $^{13}$C-NMR that Compound 1, Compound 4 and AA were reacted at 1:1:3 to produce a mixture of Compound 5 and Compound 6.

The mass average molecular weight of this compound, determined by GPC, was 600 and the viscosity at 25° C. was 70 mPa·s.

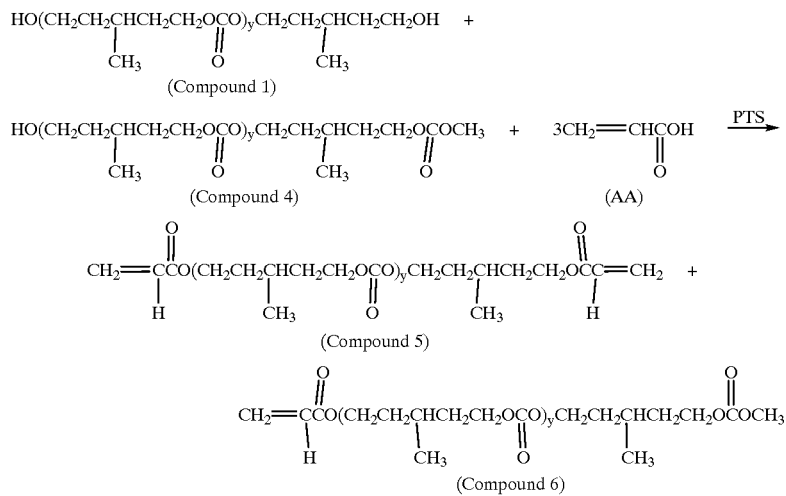

Example 4

Synthesis of Polymerizable Compound Mixture (Mixture of Compound 2 and Compound 7)

A mixture of Compound 1 and Compound 4 (1:1 by mol) and MI (produced by Showa Denko K.K.) were reacted according to the reaction formula shown below and a polymerizable compound (a mixture of Compound 2 and Compound 7) was obtained through the following procedure.

Specifically, 50.0 g of a dehydrated 1:1 (by mol) mixture of Compound 1 and Compound 4 and 25.0 g of MI were reacted in dry air at 50° C. for about 5 hours while adding thereto 0.08 g of dibutyltin dilaurate, and as a result, a colorless viscous liquid was obtained.

It was found from $^1$H-NMR and $^{13}$C-NMR that Compound 1, Compound 4 and MI were reacted at 1:1:3 to produce a mixture of Compound 2 and Compound 7.

The mass average molecular weight of this compound, determined by GPC, was 700 and the viscosity at 25° C. was 360 mPa·s.

80° C. for 60 minutes in an argon atmosphere, the composition was cured and a solid polymer electrolyte resulting from the polymerization of Compound 3 was obtained. This cured product had a residual double bond content lower than the detectable limit in the infrared spectrum and an ionic conductivity of 3.8 mS/cm (at 25° C.).

Also, when 1 g of the thus-prepared polymerizable composition was left standing at 25° C. in an argon atmosphere,

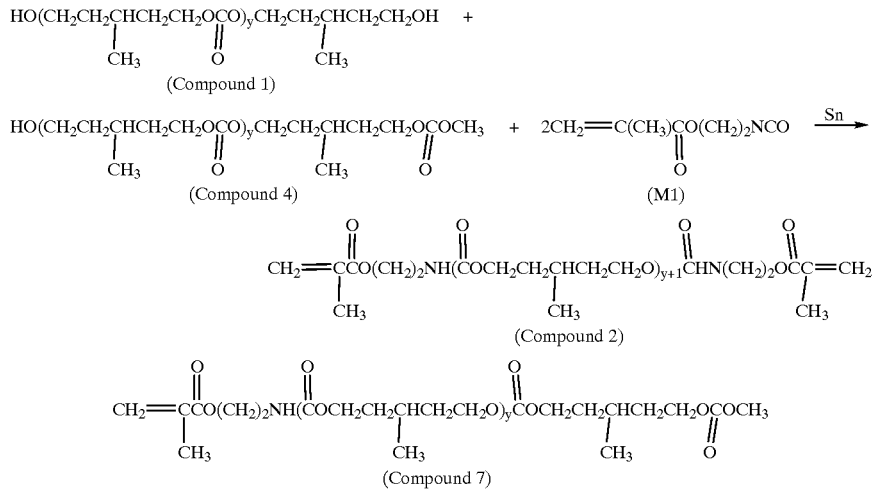

the viscosity abruptly elevated after 25 hours and the composition as a whole lost fluidity and solidified.

Example 5

Preparation of Polymerizable Composition A 1.0 g of Compound 2 synthesized in Example 1, 7.0 g of diethyl carbonate (DEC), 2.0 g of ethylene carbonate (EC), 1.0 g of LiPF$_6$, 40 mg of 2,4-diphenyl-4-methyl-1-pentene (NOFMER MSD, a trade name, produced by NOF Corp.) as a polymerization retarder and 50 mg of t-hexyl peroxypivalate (PERHEXYL PV, a trade name, produced by NOF Corp.) as a thermopolymerization initiator were thoroughly mixed in an argon atmosphere to obtain Polymerizable Composition A for a solid polymer electrolyte. This composition had an initial viscosity of 5.8 mPa·s (at 25° C.). When 1 g of this polymerizable composition was heated at 60° C. for 60 minutes in an argon atmosphere, the composition was cured and a solid polymer electrolyte resulting from the polymerization of Compound 2 was obtained. This cured product had a residual double bond content lower than the detectable limit in the infrared spectrum and an ionic conductivity of 4.7 mS/cm (at 25° C.).

Also, when 1 g of the thus-prepared polymerizable composition was left standing at 25° C. in an argon atmosphere, the viscosity abruptly elevated after 15 hours and the composition as a whole lost fluidity and solidified.

Example 6

Preparation of Polymerizable Composition B

Polymerizable Composition B for solid polymer electrolyte was obtained in the same manner as in Example 5, except that 1.0 g of Compound 3 synthesized in Example 2 was used in place of 1.0 g of Compound 2 and the amount of polymerization retarder NOFMER MSD (produced by NOF Corp.) was changed from 40 mg to 10 mg. This composition had an initial viscosity of 4.7 mPa·s (at 25° C.). When 1 g of this polymerizable composition was heated at

Example 7

Preparation of Polymerizable Composition C

Polymerizable Composition C for solid polymer electrolyte was obtained in the same manner as in Example 5, except that 1.0 g of a mixture of Compound 5 and Compound 6 synthesized in Example 3 was used in place of 1.0 g of Compound 2 and the amount of polymerization retarder NOFMER MSD (produced by NOF Corp.) was changed from 40 mg to 10 mg. This composition had an initial viscosity of 4.2 mPa·s (at 25° C.). When 1 g of this polymerizable composition was heated at 80° C. for 60 minutes in an argon atmosphere, the composition was cured and a solid polymer electrolyte resulting from the copolymerization of Compound 5 and Compound 6 was obtained. This cured product had a residual double bond content lower than the detectable limit in the infrared spectrum and an ionic conductivity of 4.0 mS/cm (at 25° C.).

Also, when 1 g of the thus-prepared polymerizable composition was left standing at 25° C. in an argon atmosphere, the viscosity abruptly elevated after 30 hours and the composition as a whole lost fluidity and solidified.

Example 8

Preparation of Polymerizable Composition D

Polymerizable Composition D for solid polymer electrolyte was obtained in the same manner as in Example 5, except that 1.0 g of a mixture of Compound 2 and Compound 7 synthesized in Example 4 was used in place of 1.0 g of Compound 2. This composition had an initial viscosity of 4.8 mPa·s (at 25° C.). When 1 g of this polymerizable composition was heated at 60° C. for 60 minutes in an argon atmosphere, the composition was cured and a solid polymer electrolyte resulting from the copolymerization of Compound 2 and Compound 7 was obtained. This cured product had a residual double bond content lower than the detectable limit in the infrared spectrum and an ionic conductivity of 4.8 mS/cm (at 25° C.).

Also, when 1 g of the thus-prepared polymerizable composition was left standing at 25° C. in an argon atmosphere, the viscosity abruptly elevated after 15 hours and the composition as a whole lost fluidity and solidified.

Example 9

Synthesis of Polymerizable Compound (Compound 9)

Carbonate-diol (produced by Nippon Polyurethane, mass average molecular weight: 500) (Compound 8) and MI (produced by Showa Denko K.K.) were reacted according to the reaction formula shown below and a polymerizable compound (Compound 9) was obtained through the following procedure.

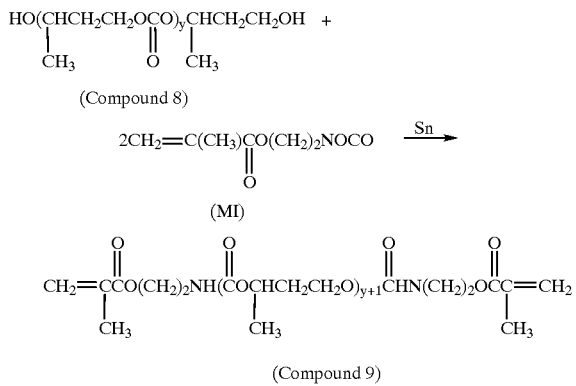

(Compound 9)

Specifically, 50.0 g of dehydrated Compound 8 (mass average molecular weight: 500, hydroxyl group value: 224 KOHmg/g, water content: 30 ppm) and 32.0 g of MI were reacted in dry air at 50° C. for about 5 hours while adding thereto 0.1 g of dibutyltin dilaurate. As a result, a colorless viscous liquid was obtained. It was found from $^1$H-NMR and $^{13}$C-NMR that Compound 8 and MI were reacted at 1:2 and since the absorption of isocyanate group of Compound 8 disappeared from the infrared absorption spectrum, a urethane bond was produced, and thus revealing the production of Compound 9. The mass average molecular weight of Compound 9, determined by GPC (gel permeation chromatography), was 800 and the viscosity at 25° C. was 3,000 mPa·s.

Example 10

Synthesis of Polymerizable Compound (Compound 10)

Compound 8 and commercially available AA were reacted according to the reaction formula shown below and a polymerizable compound (Compound 10) was obtained through the following procedure.

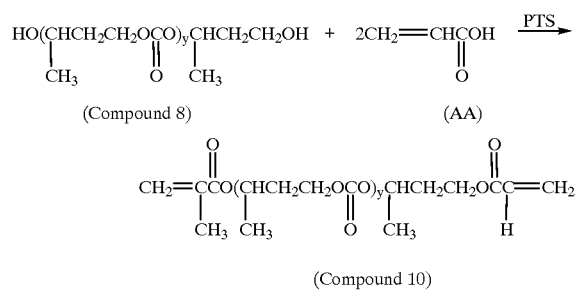

(Compound 10)

Specifically, 50.0 g of Compound 8 and 17.0 g of AA were reacted in benzene at 90° C. for about 10 hours while adding thereto 2.2 g of PTS. Thereafter, the reaction solution was extracted with chloroform and dehydrated, and as a result, a colorless viscous liquid was obtained. It was found from $^1$H-NMR and $^{13}$C-NMR that Compound 8 and AA were reacted at 1:2 to produce Compound 10.

The mass average molecular weight of this compound, determined by GPC, was 650 and the viscosity at 25° C. was 150 mPa·s.

Example 11

Preparation of Polymerizable Composition E

Polymerizable Composition E for solid polymer electrolyte was obtained in the same manner as in Example 5, except that 1.0 g of Compound 9 synthesized in Example 9 was used in place of 1.0 g of Compound 2. This composition had an initial viscosity of 5.1 mPa·s (at 25° C.). When 1 g of this polymerizable composition was heated at 60° C. for 60 minutes in an argon atmosphere, the composition was cured and a solid polymer electrolyte resulting from the polymerization of Compound 9 was obtained. This cured product had a residual double bond content lower than the detectable limit in the infrared spectrum and an ionic conductivity of 3.8 mS/cm (at 25° C.).

Also, when 1 g of the thus-prepared polymerizable composition was left standing at 25° C. in an argon atmosphere, the viscosity abruptly elevated after 25 hours and the composition as a whole lost fluidity and solidified.

Example 12

Preparation of Polymerizable Composition F

Polymerizable Composition F for solid polymer electrolyte was obtained in the same manner as in Example 5, except that 1.0 g of Compound 10 synthesized in Example 10 was used in place of 1.0 g of Compound 2 and the amount of polymerization retarder NOFMER MSD (NOF Corp.) was changed from 40 mg to 5 mg. This composition had an initial viscosity of 4.4 mPa·s (at 25° C.). When 1 g of this polymerizable composition was heated at 80° C. for 60 minutes in an argon atmosphere, the composition was cured and a solid polymer electrolyte resulting from the polymerization of Compound 10 was obtained. This cured product had a residual double bond content lower than the detectable limit in the infrared spectrum and an ionic conductivity of 3.7 mS/cm (at 25° C.).

Also, when 1 g of the thus-prepared polymerizable composition was left standing at 25° C. in an argon atmosphere, the viscosity abruptly elevated after 30 hours and the composition as a whole lost fluidity and solidified.

Comparative Example 1

Synthesis of Polymerizable Compound (Compound 12)

Carbonate-diol (produced by Nippon Polyurethane K.K., mass average molecular weight: 500) (Compound 11) and MI (produced by Showa Denko K.K.) were reacted according to the reaction formula shown below and a polymerizable compound (Compound 12) was obtained through the following procedure.

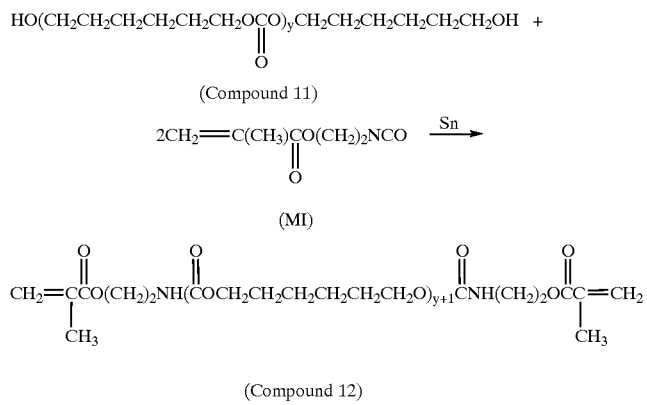

(Compound 12)

Specifically, 50.0 g of dehydrated Compound 11 (mass average molecular weight: 500, hydroxyl group value: 224 KOHmg/g, water content: 30 ppm) and 32.0 g of MI were reacted in dry air at 50° C. for about 5 hours while adding thereto 0.1 g of dibutyltin dilaurate. As a result, a colorless viscous liquid was obtained. It was found from $^1$H-NMR and $^{13}$C-NMR that Compound 11 and MI were reacted at 1:2 and since the absorption of isocyanate group of Compound 11 disappeared from the infrared absorption spectrum, a urethane bond was produced, and thus revealing the production of Compound 12. The mass average molecular weight of Compound 12, determined by GPC, was 800. This compound was solid at 25° C. and liquefied at 45° C. and the viscosity thereof was 2,000 mPa·s.

Comparative Example 2

Synthesis of Polymerizable Compound (Compound 13)

Compound 11 and commercially available acrylic acid (AA) were reacted according to the reaction formula shown below and a polymerizable compound (Compound 13) was obtained through the following procedure.

Specifically, 50.0 g of Compound 11 and 17.0 g of AA were reacted in benzene at 90° C. for about 10 hours while adding thereto 2.2 g of PTS. Thereafter, the reaction solution was washed with an aqueous NaOH solution and then dehydrated, and as a result, a colorless viscous liquid was obtained. It was found from $^1$H-NMR and $^{13}$C-NMR that Compound 1 and AA were reacted at 1:2 to produce Compound 13.

The mass average molecular weight of this compound, determined by GPC, was 650. This compound was solid at 25° C. and liquefied at 45° C. and the viscosity thereof was 220 mPa·s.

Comparative Example 3

Synthesis of Polymerizable Compound (Compound 15)

Carbonate-diol (produced by Nippon Polyurethane K.K., mass average molecular weight: 2,000) (Compound 14) and MI (produced by Showa Denko K.K.) were reacted according to the reaction formula shown below and a polymerizable compound (Compound 15) was obtained through the following procedure.

Specifically, 50.0 g of dehydrated Compound 14 (mass average molecular weight: 2,000, hydroxyl group value: 56 KOHmg/g, water content: 30 ppm) and 8.0 g of MI were reacted in dry air at 50° C. for about 5 hours while adding thereto 0.02 g of dibutyltin dilaurate, and as a result, a colorless viscous liquid was obtained. It was found from $^1$H-NMR and $^{13}$C-NMR that Compound 14 and MI were reacted at 1:2 and since the absorption of isocyanate group

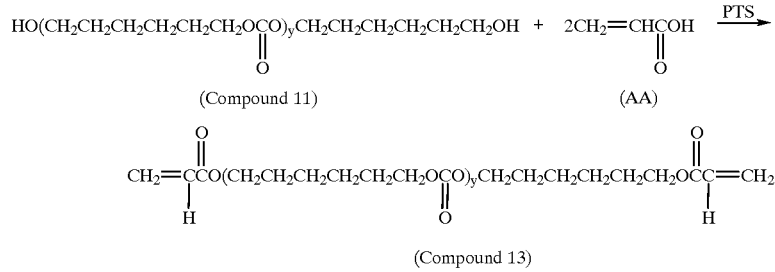

(Compound 13)

of Compound 14 disappeared from the infrared spectrum, a urethane bond was produced, and thus revealing the production of Compound 15. The mass average molecular weight of Compound 2, determined by GPC, was 2,300 and the viscosity at 25° C. was 100,000 mPa·s.

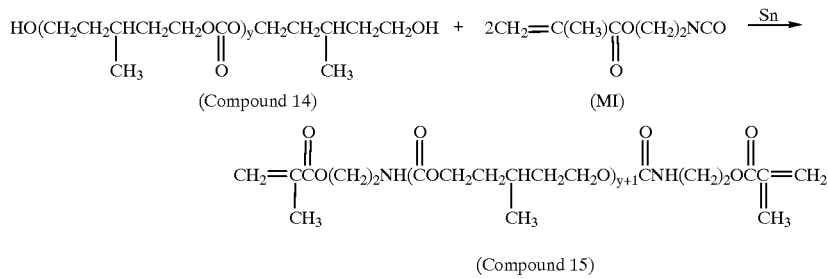

(Compound 15)

Comparative Example 4

Synthesis of Polymerizable Compound (Compound 16)

Compound 14 and commercially available AA were reacted according to the reaction formula shown below and a polymerizable compound (Compound 16) was obtained through the following procedure.

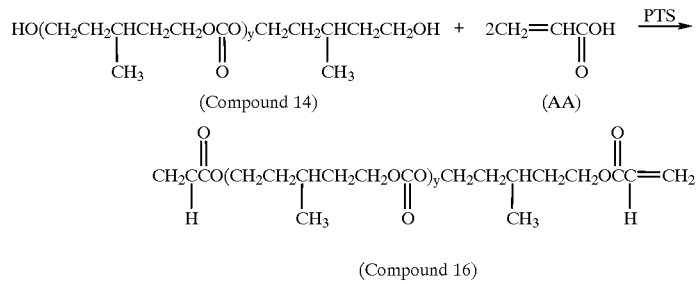

(Compound 16)

Specifically, 50.0 g of Compound 14 and 4.0 g of AA were reacted in benzene at 90° C. for about 5 hours while adding thereto 0.5 g of PTS. Thereafter, the reaction solution was extracted with chloroform and dehydrated, and as a result, a colorless viscous liquid was obtained. It was found from $^1$H-NMR and $^3$C-NMR that Compound 14 and AA were reacted at 1:2 to produce Compound 16.

The mass average molecular weight of this compound, determined by GPC, was 2,100 and the viscosity at 25° C. was 2,000 mPa·s.

Comparative Example 5

Preparation of Polymerizable Composition G

Polymerizable Composition G for solid polymer electrolyte was obtained in the same manner as in Example 5, except that 1.0 g of Compound 12 synthesized in Comparative Example 1 was used in place of 1.0 g of Compound 2. This composition had an initial viscosity of 6.7 mPa·s (at 25° C.). When 1 g of this polymerizable composition was heated at 60° C. for 60 minutes in an argon atmosphere, the composition was cured and a solid polymer electrolyte resultant from the polymerization of Compound 12 was obtained. This cured product had a residual double bond content lower than the detectable limit in the infrared spectrum and an ionic conductivity of 4.2 mS/cm (at 25° C.).

Also, when 1 g of the thus-prepared polymerizable composition was left standing at 25° C. in an argon atmosphere, the viscosity abruptly elevated after 12 hours and the composition as a whole lost fluidity and solidified.

Comparative Example 6

Preparation of Polymerizable Composition H

Polymerizable Composition H for solid polymer electrolyte was obtained in the same manner as in Example 5, except that 1.0 g of Compound 13 synthesized in Comparative Example 2 was used in place of 1.0 g of Compound 2 and the amount of polymerization retarder NOFMER MSD (NOF Corp.) was changed from 40 mg to 5 mg. This composition had an initial viscosity of 4.4 mPa·s (at 25° C.). When 1 g of this polymerizable composition was heated at 80° C. for 60 minutes in an argon atmosphere, the composition was cured and a solid polymer electrolyte resulting from the polymerization of Compound 13 was obtained. This cured product had a residual double bond content lower than the detectable limit in the infrared spectrum and an ionic conductivity of 3.4 mS/cm (at 25° C.).

Also, when 1 g of the thus-prepared polymerizable composition was left standing at 25° C. in an argon atmosphere, the viscosity abruptly elevated after 30 hours and the composition as a whole lost fluidity and solidified.

Comparative Example 7

Preparation of Polymerizable Composition I

Polymerizable Composition I for solid polymer electrolyte was obtained in the same manner as in Example 5, except that 1.0 g of Compound 15 synthesized in Comparative Example 3 was used in place of 1.0 g of Compound 2. This composition had an initial viscosity of 7.8 mPa·s (at 25°

C.). When 1 g of this polymerizable composition was heated at 60° C. for 60 minutes in an argon atmosphere, the composition was cured and a solid polymer electrolyte resulting from the polymerization of Compound 15 was obtained. This cured product had a residual double bond content lower than the detectable limit in the infrared spectrum and an ionic conductivity of 4.3 mS/cm (at 25° C.).

Also, when 1 g of the thus-prepared polymerizable composition was left standing at 25° C. in an argon atmosphere, the viscosity abruptly elevated after 30 hours and the composition as a whole lost fluidity and solidified.

Comparative Example 8

Preparation of Polymerizable Composition J

Polymerizable Composition J for solid polymer electrolyte was obtained in the same manner as in Example 5, except that 1.0 g of Compound 16 synthesized in Comparative Example 4 was used in place of 1.0 g of Compound 2 and the amount of polymerization retarder NOFMER MSD (NOF Corp.) was changed from 40 mg to 5 mg. This composition had an initial viscosity of 5.7 mPa·s (at 25° C.). When 1 g of this polymerizable composition was heated at 80° C. for 60 minutes in an argon atmosphere, the composition was cured and a solid polymer electrolyte resulting from the polymerization of Compound 16 was obtained. This cured product had a residual double bond content lower than the detectable limit in the infrared spectrum and an ionic conductivity of 3.2 mS/cm (at 25° C.).

Also, when 1 g of the thus-prepared polymerizable composition was left standing at 25° C. in an argon atmosphere, the viscosity abruptly elevated after 30 hours and the composition as a whole lost fluidity and solidified.

Example 13

Production of Lithium Cobaltate Positive Electrode 11 g of $Li_2CO_3$ and 24 g of $Co_3O_4$ were thoroughly mixed and the mixture was heated at 800° C. for 24 hours in an oxygen atmosphere and pulverized to obtain $LiCoO_2$ powder. This $LiCoO_2$ powder, acetylene black and polyvinylidene fluoride were mixed at a mass ratio of 8:1:1 and thereto, an excess N-methylpyrrolidone solution was added to obtain a gel composition.

This composition was coated on an aluminum foil of about 50 μm and formed under pressure to a thickness of about 75 μm to obtain a lithium cobaltate positive electrode sheet. This sheet was cut into a 36 mm square and used as the positive electrode for battery.

Example 14

Production of Graphite Negative Electrode

To a 8.6:0.4:1.0 (by mass) mixture of MCMB graphite (produced by Osaka Gas Co., Ltd.), vapor grown graphite fiber (produced by Showa Denko K.K., average fiber diameter: 0.3 μm, average fiber length: 2.0 μm, a product heat-treated at 2,700° C.) and polyvinylidene fluoride, an excess N-methylpyrrolidone solution was added to obtain a gel composition. This composition was coated on a copper foil of about 50 μm and formed under pressure to a thickness of about 85 μm to obtain a graphite negative electrode sheet. This sheet was cut into a 40 mm square and used as the negative electrode for battery.

Example 15

Production of Solid Li Ion Secondary Battery

Within a glove box in an argon atmosphere, a sheet-like graphite negative electrode similar to the sheet produced in Example 14, a sheet-like lithium cobaltate positive electrode similar to the sheet produced in Example 13 and a 42 mm-square polyolefin microporous film were left standing in Polymerizable Composition A prepared in Example 5 and impregnated with the composition. Thereafter, the positive electrode and the negative electrode were laminated through the microporous film so that the microporous film slightly protruded from the edges (four sides) of the positive and negative electrodes. These were placed in a bag (armor body) made of a Polypropylene (PP)/Al/Polyethylene terephthalate (PET) three-layer laminate and after heat-fusing to seal the bag while applying a pressure from both surfaces using 1.1 mm-thick glass plates, the polymerizable composition was cured by heating it at 60° C. for 120 minutes to obtain a solid battery in which solid polymer electrolyte is compounded in electrodes and separator.

This battery was charged and discharged with a working voltage of 2.75 to 4.2 V and an electric current of 7 mA at 25° C. and −20° C., and as a result, the maximum discharge capacity was 32.5 mAh and 18.8 mAh, respectively. At this time, the charge-discharge coulombic efficiency was almost 100%.

The battery was repeatedly charged and discharged at 25° C., a working voltage of 2.75 to 4.2 V, a charge current of 7 mA and a discharge current of 35 mA. As a result, the maximum discharge capacity was 30.5 mAh and, even after working in excess of 300 cycles, the capacity was 70% or more of the initial capacity and not extremely reduced.

Examples 16 to 20

Production of Solid Li Ion Secondary Battery

Solid batteries in which solid polymer electrolyte within electrodes and separator was compounded were obtained in the same manner as in Example 15, except that Polymerizable Composition B, C, D, E or F prepared in Example 6, 7, 8, 11 or 12, respectively, were used in place of Polymerizable Composition A used in Example 15. However, the time period for allowing the polymerizable composition to impregnate into positive and negative electrodes and separator was selected to ensure the impregnation according to the viscosity of each composition.

These batteries were each charged and discharged with a working voltage of 2.75 to 4.2 V and an electric current of 7 mA at 25° C. and −20° C., and found to have maximum discharge capacity and charge-discharge coulombic efficiency shown in Table 1.

Also, each battery was repeatedly charged and discharged at 25° C., a working voltage of 2.75 to 4.2 V, a charge current of 7 mA and a discharge current of 35 mA, and found to have maximum discharge capacity and capacity maintenance percentage (ratio to the initial capacity) after 300 cycles shown in Table 1.

Comparative Examples 9 to 12

Production of Solid Li Ion Secondary Battery

Solid batteries in which the polymerizable composition was cured and in which a solid polymer electrolyte within electrodes and separator was compounded, were obtained in the same manner as in Example 15, except that Polymerizable Composition G, H, I or J prepared in Comparative Example 5, 6, 7 or 8, respectively, were used in place of Polymerizable Composition A used in Example 15. However, the time period for allowing the polymerizable composition to impregnate into positive and negative electrodes and separator was selected to ensure the impregnation according to the viscosity of each composition.

These batteries each was charged and discharged with a working voltage of 2.75 to 4.2 V and an electric current of 7 mA at 25° C. and 20° C., and found to have maximum discharge capacity shown in Table 2.

Also, each battery was repeatedly charged and discharged at 25° C., a working voltage of 2.75 to 4.2 V, a charge current of 7 mA and a discharge current of 35 mA, and found to have maximum discharge capacity and capacity maintenance percentage (ratio to the initial capacity) after 300 cycles shown in Table 2.

TABLE 1

Performance of Solid Li Ion,Secondary Battery

| Example | Impregnation Time (hr) | Capacity at 7 mA (mAh) 25° C. | Capacity at 7 mA (mAh) −20° C. | Maximum Discharge Capacity | Capacity (mAh) at 25° C. · 35 mA Capacity After 300 Cycles |
|---|---|---|---|---|---|
| 15 | 6 | 32.5 | 16.5 | 30.5 | 21.4(70%) |
| 16 | 4 | 32.5 | 18.0 | 30.0 | 22.5(75%) |
| 17 | 3 | 32.5 | 18.5 | 30.0 | 21.0(70%) |
| 18 | 5 | 32.5 | 17.0 | 31.0 | 22.3(72%) |
| 19 | 5 | 32.5 | 17.0 | 31.0 | 21.0(68%) |
| 20 | 4 | 32.5 | 18.0 | 29.5 | 22.1(75%) |

TABLE 2

Performance of Solid Li Ion Secondary Battery

| Comparative Example | Impregnation Time (hr) | Discharge Capacity at 7 mA (mAh) 25° C. | Discharge Capacity at 7 mA (mAh) −20° C. | Maximum Discharge Capacity | Capacity (mAh) at 25° C. · 35 mA Capacity After 300 Cycles |
|---|---|---|---|---|---|
| 9 | 10 | 30.0 | 12.0 | 29.5 | 19.2(65%) |
| 10 | 4 | 32.5 | 14.0 | 26.0 | 18.2(70%) |
| 11 | 15 | 28.0 | 12.5 | 27.0 | 16.2(60%) |
| 12 | 5 | 30.0 | 13.5 | 25.5 | 15.3(60%) |

Example 21

Preparation of Polymerizable Composition K 1.0 g a mixture (1:1 by mol) of Compound 5 and Compound 6 synthesized in Example 3, 9.0 g of propylene carbonate (PC), 2.0 g of triethylmethylammonium tetrafluoroborate (TEMABF$_4$), 20 mg of polymerization retarder NOFMER MSD (produced by NOF Corp.) and 50 mg of thermopolymerization initiator PERHEXYL PV (produced by NOF Corp.) were thoroughly mixed in an argon atmosphere to obtain Polymerizable Composition K for a solid polymer electrolyte. This composition had an initial viscosity of 6.3 mPa·s (at 25° C.). When 1 g of this polymerizable composition was heated at 80° C. for 60 minutes in an argon atmosphere, the composition was cured and a solid polymer electrolyte resulting from the copolymerization of Compound 5 and Compound 6 was obtained. This cured product had a residual double bond content lower than the detectable limit in the infrared spectrum and an ionic conductivity of 14.1 mS/cm (at 25° C.).

Also, when 1 g of the thus-prepared polymerizable composition was left standing at 25° C. in an argon atmosphere, the viscosity abruptly elevated after 20 hours and the composition as a whole lost fluidity and solidified.

Example 22

Production of Active Carbon Electrode

An excess N-methylpyrrolidone solution was added to a 8.6:0.4:1.0 (by mass) mixture of steam reactivation active carbon (specific surface area: 2,230 m$^2$/g, average particle size: 7 μm, pore volume: 0.7 ml/g) as a phenol resin calcined product, vapor grown graphite fiber (produced by Showa Denko K.K., average fiber diameter: 0.3 μm, average fiber length: 2.0 μm, a product heat-treated at 2,700° C.) and polyvinylidene fluoride, to obtain a gel composition. This composition was coated on an aluminum foil of about 25 μm and formed under pressure to a thickness of about 150 μm to obtain an active carbon electrode sheet. This sheet was cut into a 10 mm square and vacuum dried at 100° C. for 10 hours to obtain an active carbon electrode (230.0 mg) for electric double-layer capacitor.

Example 23

Production of Solid Electric Double-layer Capacitor

Within a glove box in an argon atmosphere, two sheets of active carbon electrodes (230.0 mg, 40 mm square) produced in Example 22 and a Teflon-made microporous film separator (42 mm square, 25 μm thickness, produced by Mitsui FLOROCHEMICAL) were left standing in Polymerizable Composition K prepared in Example 21 at room temperature for 8 hours and impregnated with the composition. Thereafter, these two sheets of electrodes were laminated with an interposition of microporous film separator so that the microporous film slightly protruded from the edges (four sides) of two sheets of electrodes. These were placed in a bag (armor body) made of a PP/Al/PET three-layer laminate and after heat-fusing to seal the bag while applying a pressure from both surfaces using 1.1 mm-thick glass plates, the polymerizable composition was cured by heating it at 60° C. for 120 minutes to obtain a solid electric double-layer capacitor, where the solid polymer electrolyte was compounded in electrodes and separator.

This capacitor was charged and discharged at 25° C. and −20° C., a working voltage of 0 to 2.5 V and an electric current of 7 mA, and as a result, the maximum capacitance was 9.1 F and 6.6 F, respectively. Furthermore, the capacitor was charged and discharged at 25° C. and 14 mA, and as a result, the maximum capacitance was 8.9 F. Thereafter, the charge and discharge were repeated 100 times but the capacitance was scarcely changed.

Example 24

Preparation of Polymerizable Composition L 1.0 g of a mixture (1:1 by mol) of Compound 5 and Compound 6 synthesized in Example 3, 9.0 g of propylene carbonate (PC), 1.0 g of LiBF$_4$, 5 mg of polymerization retarder NOFMER MSD (produced by NOF Corp.) and 50 mg of thermopolymerization initiator PERHEXYL PV (produced by NOF Corp.) were thoroughly mixed in an argon atmosphere to obtain Polymerizable Composition L for a solid polymer electrolyte. This composition had an initial viscosity of 4.5 mPa·s (at 25° C.). When 1 g of this polymerizable composition was heated at 80° C. for 60 minutes in an argon atmosphere, the composition was cured and a solid polymer electrolyte resulting from the copolymerization of Compound 5 and Compound 6 was obtained. This cured product had a residual double bond content lower than the detectable limit in the infrared spectrum and an ionic conductivity of 5.0 mS/cm (at 25° C.).

Also, when 1 g of the thus-prepared polymerizable composition was left standing at 25° C. in an argon atmosphere, the viscosity abruptly elevated after 25 hours and the composition as a whole lost fluidity and solidified.

Example 25

Manufacture of WO$_3$-made EC Electrode

On an electrode comprising an ITO glass (produced by Matsuzaki Shinku K.K.) cut into 1.2×1.2 cm with the edges being covered to have an ITO exposed area of 1×1 cm, WO$_3$ was vacuum deposited using tantalum boat member by a resistance heating method at $10^{-5}$ to $10^{-6}$ Torr ($1.33 \times 10^{-3}$ to $1.33 \times 10^{-4}$ Pa) to obtain WO$_3$ electrode. The obtained WO$_3$ film had a thickness of about 1,000 Å ($1 \times 10^{-7}$ m) and a density of about 5 g/cm$^3$.

Example 26

Manufacture of Polyaniline (PAn)-made EC Electrode

On an electrode comprising ITO glass (produced by Matsuzaki Shinku K.K.) cut into 1.2×1.2 cm, potential scanning was repeated at a scanning speed of 0.2 V/sec in the range from −0.2 to 0.8 V vs. SCE using an aqueous 1 mol hydrochloric acid solution containing 0.5 mol aniline as the electrolytic solution and an ITO glass of 2×2 cm as the counter electrode, whereby a doped green electrolytically polymerized PAn film of about 5,000 Å thickness was manufactured. This film was thoroughly washed with aqueous ammonia and distilled water, reduced with hydrazine and vacuum dried at 100° C. for about 3 hours to obtain an undoped white PAn electrode.

Example 27

Manufacture of Electrochromic Device (ECD)

Within a glove box in an argon atmosphere, the edge part within about 1 mm around of the PAn electrode (1.2 cm-square) produced in Example 26 was coated with a polyimide film spacer. Thereafter, the polymerizable composition prepared in Example 24 was coated on the PAn electrode and WO$_3$ electrode produced in Example 25 was stacked thereon and heated at 60° C. for 120 minutes. By sealing the edge part with an epoxy resin, an ECD shown in FIG. 3 was manufactured. This ECD was driven with an injected electricity of 6 mC/cm$^2$ at a working voltage of −2 to 2 V, and as a result, electrochromism of deep blue/pale blue was exhibited and the response seed was about 100 msec. Even when the driving was repeated 200 times under these conditions, the color tone and response speed were not changed.

The highly ion conductive solid polymer electrolyte comprising a polymer having a carbonate group as a main component and an electrolyte salt of the present invention has high ionic conductivity, excellent electrochemical stability and good durability. By introducing a branched chain, excellent processability and compounding property with other materials are ensured when the solid polymer electrolyte of the present invention is used as an electrochemical device. In particular, when the carbonate-based solid polymer electrolyte of the present invention is obtained by polymerizing a low molecular weight polymerizable compound having a branched carbonate structure, compounding with various materials can be performed before polymerization, thereby improving processability and compounding property.

The battery, electric double-layer capacitor and ECD using the solid polymer electrolyte of the present invention are free from fears of liquid leakage, and are favored with excellent reliability and safety over a long period of time and has wide freeness in shape such as thin type.

The battery of the present invention uses the above-described solid polymer electrolyte and therefore, can be easily formed into a film. Also, the battery can be easily and simply compounded with respective elements such as positive electrode and/or negative electrode and/or separator so that the battery can work with high capacity and high current, and ensures long life and high reliability.

The battery of the present invention can work with high capacity and high current as a solid battery or can ensure good cycle property and excellent safety and reliability so that the battery can be used as a power source for electrical products, such as main power source or backup power source of portable appliances, or as a large-sized power source for electric cars or road leveling. Furthermore, the battery can be easily formed into a thin film and therefore, can be used as a paper battery for an identification card or the like.

The electric double-layer capacitor of the present invention uses the above-described solid polymer electrolyte so that the capacitor can have high output voltage, large takeout current, good processability, long life and excellent reliability.

Furthermore, the electric double-layer capacitor of the present invention is a solid electric double-layer capacitor capable of working with high voltage, high capacitance and high current, and ensuring good cycle property, excellent safety and high reliability compared with conventional solid electric double-layer capacitors. Accordingly, the capacitor can be used not only as a backup power source, but also as a power source for various electrical products by using it in combination with a compact battery. In addition, the electric double-layer capacitor of the present invention has excellent processability such as formation into thin film and therefore, can be applied to uses other than those of conventional solid-state electric double-layer capacitors.

While the invention has been described in detail and with reference to specific embodiments thereof, it will be apparent to one skilled in the art that various changes and modifications can be made therein without departing from the spirit and scope thereof.

What is claimed is:

1. A solid polymer electrolyte comprising a polymer compound having a branched carbonate structure represented by formula (1) as a partial structure and at least one electrolyte salt:

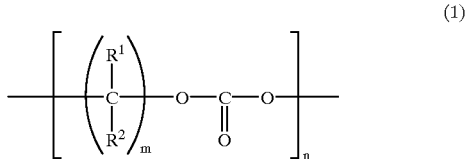

(1)

wherein each R$^1$ and R$^2$ independently represents a hydrogen atom, a linear, branched or cyclic alkyl group having from 1 to 10 carbon atoms, a linear, branched or cyclic alkoxy group having from 1 to 10 carbon atoms or a linear, branched or cyclic alkoxyalkyl group having from 1 to 10 carbon atoms, m represents an integer of 3 to 10, n represents an integer of 1 to 500, and each $R^1$ and $R^2$ and each value of m and n can be the same or different, provided that $R^1$ or $R^2$ present in plurality within the same molecule are not a hydrogen atom at the same time.

2. A battery comprising a solid polymer electrolyte as claimed in claim 1, a positive electrode and a negative electrode.

3. The battery as claimed in claim 2, which is a lithium primary or lithium secondary battery comprising at least one electrolyte salt selected from the group consisting of $LiPF_6$, $LiBF_4$, $LiAsF_6$ and $LiN(A-SO_2)_2$, wherein A represents a perfluoroalkyl group having from 1 to 10 carbon atoms.

4. A solid polymer electrolyte comprising a polymer compound having a branched carbonate structure represented by formula (2) as a partial structure and at least one electrolyte salt:

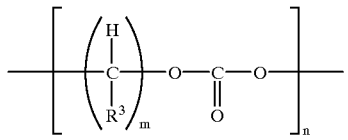

(2)

wherein $R^3$ represents a hydrogen atom, a linear, branched or cyclic alkyl group having from 1 to 10 carbon atoms, a linear, branched or cyclic alkoxy group having from 1 to 10 carbon atoms or a linear, branched or cyclic alkoxyalkyl group having from 1 to 10 carbon atoms, m represents an integer of 3 to 10, n represents an integer of 1 to 500, and each $R^3$ and each value of m and n can be the same or different, provided that $R^3$ present in plurality within the same molecule are not a hydrogen atom at the same time.

5. A solid polymer electrolyte as described in claim 1 or 4, wherein the polymer compound having a branched carbonate structure has a polymerizable functional group represented by the following formula (3) and/or (4):

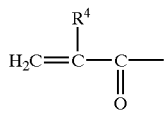

(3)

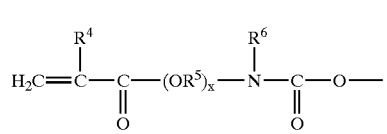

(4)

wherein $R^4$ represents a hydrogen atom or a linear, branched or cyclic alkyl group having from 1 to 10 carbon atoms, $R^6$ represents a hydrogen atom, a linear, branched or cyclic alkyl group having from 1 to 10 carbon atoms, a linear, branched or cyclic alkoxy group having from 1 to 10 carbon atoms or a linear, branched or cyclic alkoxyalkyl group having from 1 to 10 carbon atoms, $R^5$ represents a divalent group which can contain a heteroatom and can have a linear, branched or cyclic structure, and x represents 0 or 1, provided that $R^4$, $R^5$, $R^6$ or x present in plurality within the same molecule can be the same or different.

6. The solid polymer electrolyte as claimed in claim 5, wherein the polymerizable compound has a mass average molecular weight of about 100 to about 3,000.

7. The solid polymer electrolyte as claimed in claim 5, wherein the polymerizable compound is almost liquid at room temperature and a viscosity thereof is about 5,000 mPa·S (25° C.) or less.

8. The solid polymer electrolyte as claimed in claim 1 or 4, which further comprises at least one organic solvent.

9. The solid polymer electrolyte as claimed in claim 8, wherein the organic solvent is at least one selected from the group consisting of carbonates, aliphatic esters, ethers, lactones, sulfoxides and amides.

10. The solid polymer electrolyte as claimed in claim 1 or 4, wherein the electrolyte salt is at least one selected from the group consisting of an alkali metal salt, a quaternary ammonium salt and a quaternary phosphonium salt.

11. A polymerizable composition for a solid polymer electrolyte, comprising at least one polymerizable compound having a branched carbonate structure, represented by formula (1) as a partial structure:

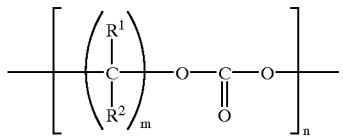

(1)

wherein each $R^1$ and $R^2$ independently represents a hydrogen atom, a linear, branched or cyclic alkyl group having from 1 to 10 carbon atoms, a linear, branched or cyclic alkoxy group having from 1 to 10 carbon atoms or a linear, branched or cyclic alkoxyalkyl group having from 1 to 10 carbon atoms, m represents an integer of 3 to 10, n represents an integer of 1 to 500, and each $R^1$ and $R^2$ and each value of m and n can be the same or different, provided that $R^1$ or $R^2$ present in plurality within the same molecule are not a hydrogen atom at the same time, or represented by formula (2) as a partial structure:

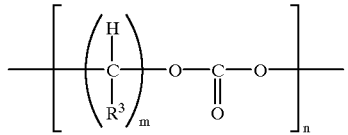

(2)

wherein $R^3$ represents a hydrogen atom, a linear, branched or cyclic alkyl group having from 1 to 10 carbon atoms, a linear, branched or cyclic alkoxy group having from 1 to 10 carbon atoms or a linear, branched or cyclic alkoxyalkyl group having from 1 to 10 carbon atoms, m represents an integer of 3 to 10, n represents an integer of 1 to 500, and each $R^3$ and $R^2$ and each value of m and n can be the same or different, provided that $R^3$ present in plurality within the same molecule are not a hydrogen atom at the same time, and wherein the polymerizable compound having a branched carbonate structure has a polymerizable functional group represented by the following formula (3) and/or (4):

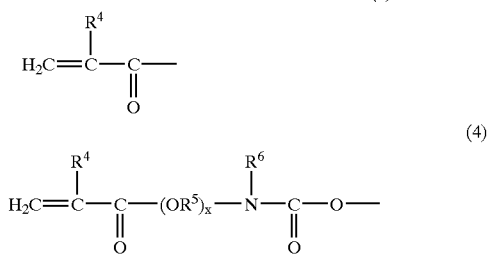

wherein R⁴ represents a hydrogen atom or a linear, branched or cyclic alkyl group having from 1 to 10 carbon atoms, R⁶ represents a hydrogen atom, a linear, branched or cyclic alkyl group having from 1 to 10 carbon atoms, a linear, branched or cyclic alkoxy group having from 1 to 10 carbon atoms or a linear, branched or cyclic alkoxyalkyl group having from 1 to 10 carbon atoms, R⁵ represents a divalent group which can contain a heteroatom and can have a linear, branched or cyclic structure, and x represents 0 or 1, provided that R⁴, R⁵, R⁶ or x present in plurality within the same molecule can be the same or different and at least one electrolyte salt.

12. The polymerizable composition for a solid polymer electrolyte as claimed in claim 11, further comprising at least one organic solvent.

13. A solid polymer electrolyte obtained by polymerizing the polymerizable composition claimed in claim 12.

14. The polymerizable composition for solid polymer electrolytes as claimed in claim 12, wherein the organic solvent is at least one selected from the group consisting of carbonates, aliphatic esters, ethers, lactones, sulfoxides and amides.

15. The polymerizable composition for a solid polymer electrolyte as Claimed in claim 12, wherein a viscosity is about 6.0 mPa·S (25° C.) or less.

16. A solid polymer electrolyte obtained by polymerizing the polymerizable composition claimed in claim 15.

17. A solid polymer electrolyte obtained by polymerizing the polymerizable composition claimed in claim 11.

18. The polymerizable composition for a solid polymer electrolyte as claimed in claim 11, wherein the electrolyte salt is at least one selected from the group consisting of an alkali metal salt, a quaternary ammonium salt and a quaternary phosphonium salt.

* * * * *